United States Patent
Sunaga et al.

(10) Patent No.: US 7,135,242 B2
(45) Date of Patent: Nov. 14, 2006

(54) ELECTROLUMINESCENT POLYMER, BISFLUORENYLSILANE COMPOUND AND ORGANIC ELECTROLUMINESCENT ELEMENT

(75) Inventors: Tomoyasu Sunaga, Kanuma (JP); Junichi Ishll, Kanuma (JP); Susumu Yanagibori, Kanuma (JP); Miyuki Tsukioka, Kanuma (JP)

(73) Assignees: Sony Corporation, Tokyo (JP); Sony Chemical & Information Device Corporation, Tokyo (JP)

( * ) Notice: Subject to any disclaimer, the term of this patent is extended or adjusted under 35 U.S.C. 154(b) by 66 days.

(21) Appl. No.: 10/496,875

(22) PCT Filed: Oct. 14, 2003

(86) PCT No.: PCT/JP03/13136

§ 371 (c)(1),
(2), (4) Date: May 26, 2004

(87) PCT Pub. No.: WO2004/035652

PCT Pub. Date: Apr. 29, 2004

(65) Prior Publication Data

US 2005/0079382 A1    Apr. 14, 2005

(30) Foreign Application Priority Data

Oct. 15, 2002    (JP)    ............................. 2002-301145
Oct. 8, 2003     (JP)    ............................. 2003-350152

(51) Int. Cl.
   $H05B\ 33/14$    (2006.01)
   $C09K\ 11/06$   (2006.01)
   $C07F\ 7/08$    (2006.01)

(52) U.S. Cl. .................... 428/690; 428/914; 313/504; 257/40; 556/430; 556/465; 528/31; 528/33; 528/40; 528/43; 252/301.35

(58) Field of Classification Search ................ 428/690, 428/917; 252/301.35; 313/504; 556/465, 556/430; 528/40, 31, 33, 43; 257/40
See application file for complete search history.

(56) References Cited

U.S. PATENT DOCUMENTS 6,558,819 B1 *    5/2003    Igarashi ...................... 428/690

FOREIGN PATENT DOCUMENTS

| JP | A 9-78060 | 3/1997 |
| JP | A 2001-55447 | 2/2001 |
| JP | A 2001-335639 | 12/2001 |
| WO | WO 00/22026 | 4/2000 |

OTHER PUBLICATIONS

S. Yamaguchi, et al., Toward New Materials for Organic Electroluminescent Devices: Synthesis, Structures, and Properties of a Series of 2,5-Diaryl-3,4-diphenylsiloles, Chem. Eur. Journal, 2000, vol. 6, pp. 1683-1692, No. 9.

Y. Ohmori, et al., Blue Electroluminescent Diodes Utilizing Poly(alkylfluorene), Japanese Journal of Applied Physics, vol. 30, No. 11B, Nov. 1991, pp. L 1941-L 1943.

* cited by examiner

Primary Examiner—Rena Dye
Assistant Examiner—Camie S. Thompson
(74) Attorney, Agent, or Firm—Oliff & Berridge, PLC

(57) ABSTRACT

An electroluminescent polymer which has repeating units represented by formula (1) is obtained by polymerizing a bisfluorenylsilane compound which has specified substituent groups.

Comparative Example 1 Preior to Heat Treatment

Comparative Example 1 Following Heat Treatment

In spite of the fact that this electroluminescent polymer is a π-σ conjugated type fluorene polymer, the deterioration in the color purity of EL caused by excimer formation is suppressed, so that the color purity of blue emitted light in particular is extremely high. This electroluminescent polymer is extremely useful as a light-emitting material in organic electroluminescent elements.

16 Claims, 13 Drawing Sheets

Comparative Example 1 Proior to Heat Treatment

Comparative Example 1 Following Heat Treatment

Example 7 Prior to Heat Treatment

Example 7 Following Heat Treatment

Example 8 Prior to Heat Treatment

Example 8 Following Heat Treatment

ELECTROLUMINESCENT POLYMER, BISFLUORENYLSILANE COMPOUND AND ORGANIC ELECTROLUMINESCENT ELEMENT

TECHNICAL FIELD

The present invention relates to an electroluminescent (EL) polymer which is useful as a light-emitting layer material in an organic EL element, a bisfluorenylsilane compound which is a raw material used in the manufacture of this EL polymer, and an organic EL element using this EL polymer.

BACKGROUND ART

Conventionally, π conjugated polymers and σ conjugated polymers have been known as organic EL materials which are used to construct the light-emitting layers of organic EL elements.

Polymers represented by poly(paraphenylenevinylene)s (PPV), poly(paraphenylene)s (PPP) and the like are widely utilized as π conjugated polymers. Among such π conjugated polymers, poly(9,9-dialkylfluorene)s (PDAF) have actually been used as polymers that show blue light emission (Y. Ohmori et al., Jpn. J. Appl. Phys., 1991, 30, L1941).

Furthermore, the use of polysilanes (Japanese Patent Application Laid-Open No. 9-78060), polysiloles (S. Yamaguchi et al., Chem. Eur. J., 2000, 6, 1683) and the like as σ conjugated polymers has also been proposed.

Furthermore, polymers comprising fluorene derivative units (π conjugated system) and diarylenesilane derivative units (σ conjugated system) have also been proposed as π-σ conjugated polymers that have a π conjugated system and a σ conjugated system in a single molecule (Japanese Patent Application Laid-Open No. 2001-55447).

However, in the case of π conjugated polymers, the following problem has been encountered: namely, the conjugate length system becomes long when the degree of polymerization increases; as a result, the HOMO-LUMO energy gap (Eg) becomes small, so that the emitted light is shifted toward the red end. Especially in the case of blue light-emitting polymers, the problem of a deterioration in the color purity has been encountered. Furthermore, since the proportion of aromatic rings in π conjugated polymers is extremely high, it cannot be said that the solubility of such polymers in organic solvents is sufficient; as a result, the following problem has also been encountered: specifically, there are cases in which simple film forming methods such as spin coating and the like cannot be used.

Furthermore, in the case of σ conjugated polymers, the electron transporting ability and electron injection ability of polymers are insufficient even though Hall mobility is large.

Meanwhile, in the case of π-σ conjugated polymers, although the drawbacks of σ conjugated polymers can generally be ameliorated, blue emitted light with a high color purity still cannot be obtained.

Objects of the present invention include the provision of a novel π-σ conjugated polymer in which the color purity of blue emitted light in particular is extremely high, the provision of a novel raw material for the manufacture of this π-σ conjugated polymer, and the provision of an organic EL element which uses this π-σ conjugated polymer.

DISCLOSURE OF THE INVENTION

The present inventors discovered that the abovementioned objects can be achieved by means of a polymer obtained by polymerizing a bisfluorenylsilane compound which has specified substituent groups. This discovery led to the perfection of the present invention.

Specifically, the present invention provides an electroluminescent polymer which has repeating units represented by formula (1).

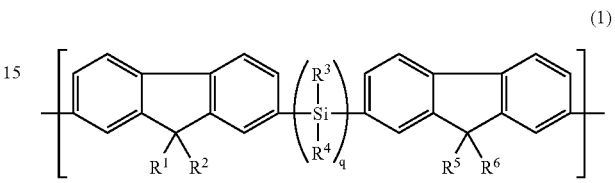

(1)

In the above formula, $R^1$, $R^2$, $R^5$ and $R^6$ each independently indicate a hydrogen atom or substituent group, $R^3$ and $R^4$ each independently indicate an aryl group or alkyl group, and q is 1 or 2.

Furthermore, the present invention provides a bisfluorenylsilane compound which is represented by formula (3).

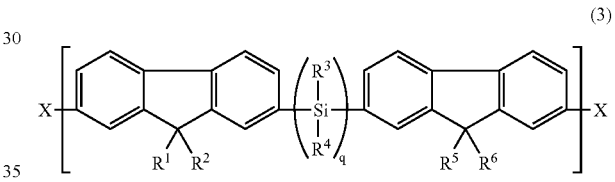

(3)

In the above formula, $R^1$, $R^2$, $R^5$ and $R^6$ each independently indicate a hydrogen atom or substituent group, $R^3$ and $R^4$ each independently indicate an aryl group or alkyl group, q is 1 or 2, and X is a halogen atom.

Furthermore, the present invention provides an organic electroluminescent element in which a light-emitting layer comprising the abovementioned electroluminescent polymer is clamped between a pair of electrodes.

BEST MODE FOR CARRYING OUT THE INVENTION

Figure 1A:
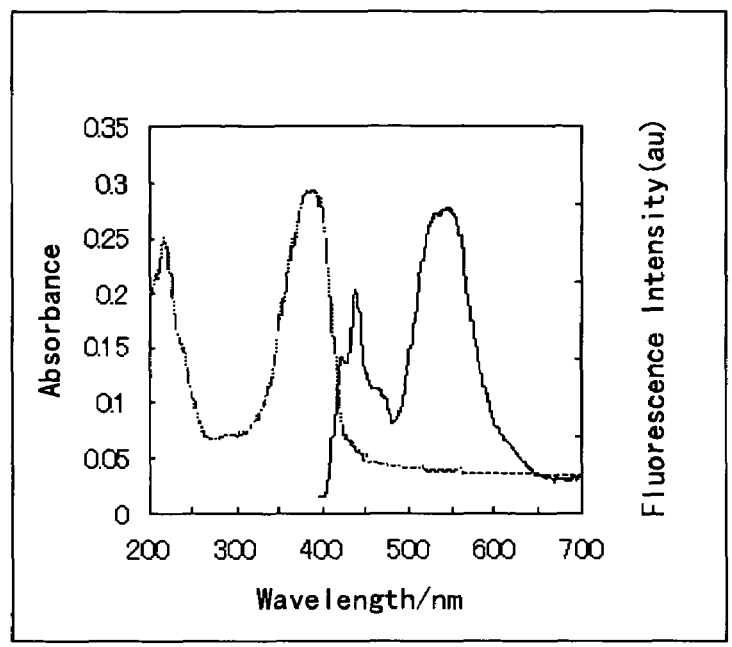
FIG. 1A shows the ultraviolet-visible absorption spectrum (fluorescent spectrum) of the poly(9,9-dioctylfluorene) film of Comparative Example 1 prior to heat treatment.
Figure 1B:
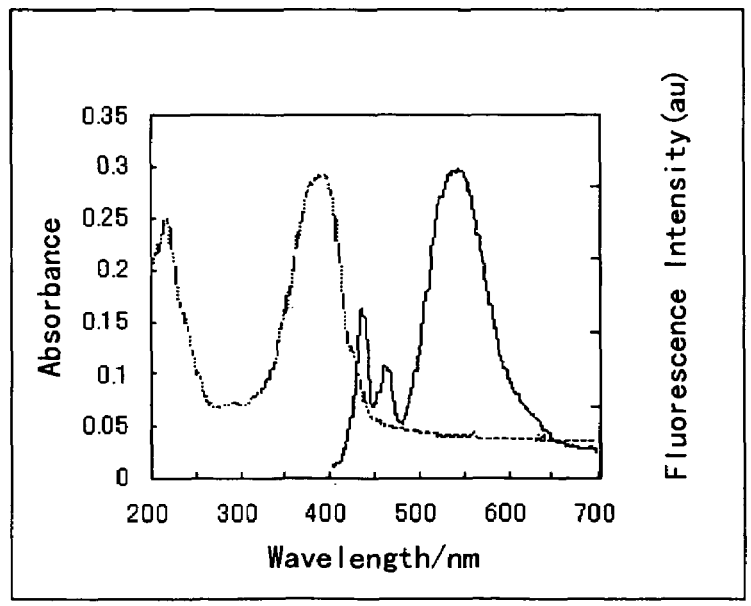
FIG. 1B shows the ultraviolet-visible absorption spectrum (fluorescent spectrum) of the same film following heat treatment.
Figure 2A:
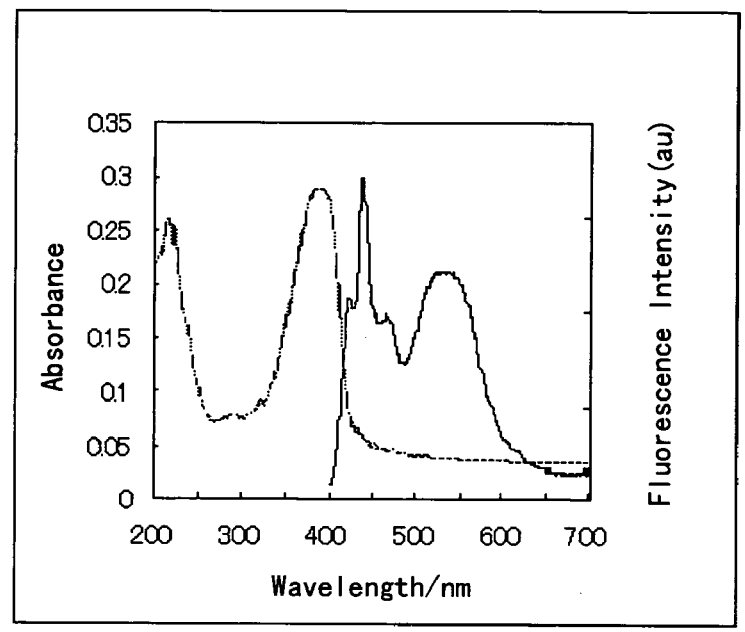
FIG. 2A shows the ultraviolet-visible absorption spectrum (fluorescent spectrum) of the EL polymer film of Example 6 (containing the repeating unit of formula (4) (bisfluorenyldiphenylsilane) at the rate of 10 mol %) prior to heat treatment and FIG. 2B shows the ultraviolet-visible absorption spectrum (fluorescent spectrum) of the same film following heat treatment.
Figure 2B:
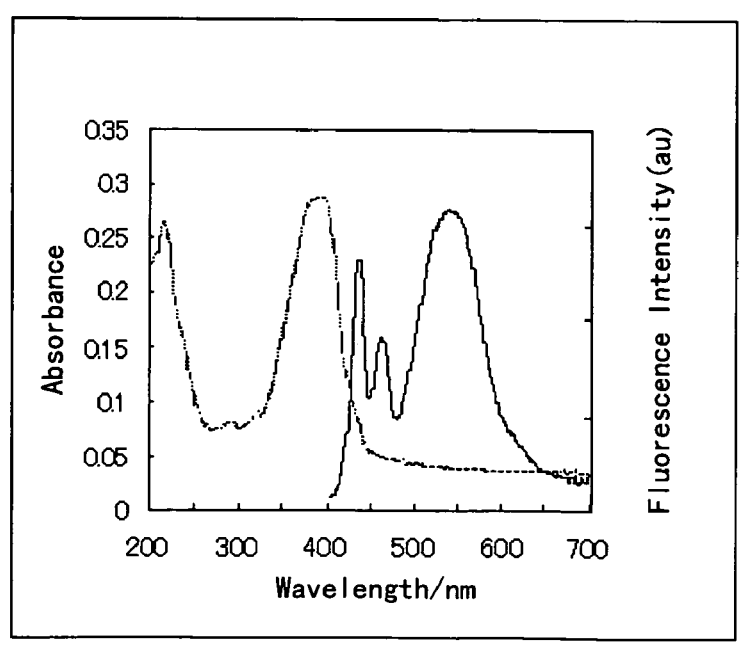
Figure 3A:
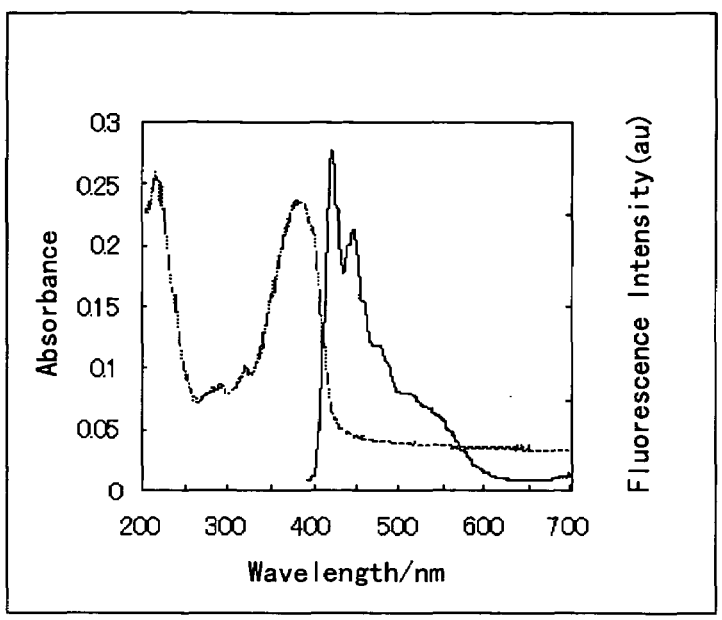
FIG. 3A shows the ultraviolet-visible absorption spectrum (fluorescent spectrum) of the EL polymer film of Example 7 (containing the repeating unit of formula (4) (bisfluorenyldiphenylsilane) at the rate of 25 mol %) prior to heat treatment and FIG. 3B shows the ultraviolet-visible absorption spectrum (fluorescent spectrum) of the same film following heat treatment.
Figure 3B:
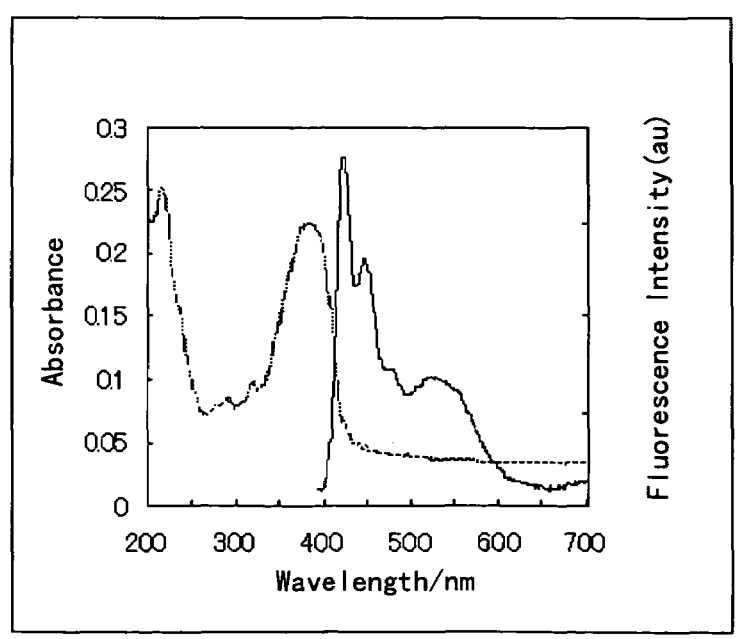
Figure 4A:
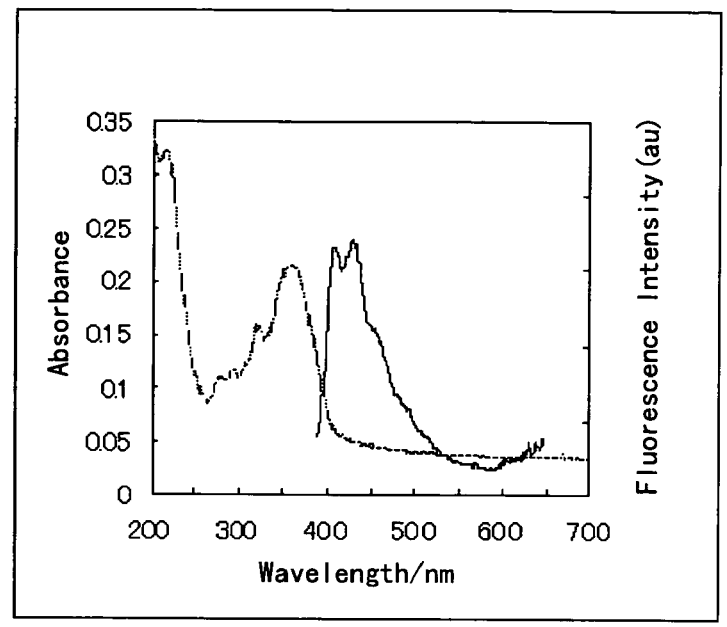
FIG. 4A shows the ultraviolet-visible absorption spectrum (fluorescent spectrum) of the EL polymer film of Example 8 (containing the repeating unit of formula (4) (bisfluorenyldiphenylsilane) at the rate of 50 mol %) prior to heat treatment and FIG. 4B shows and the ultraviolet-visible absorption spectrum (fluorescent spectrum) of the same film following heat treatment.
Figure 4B:
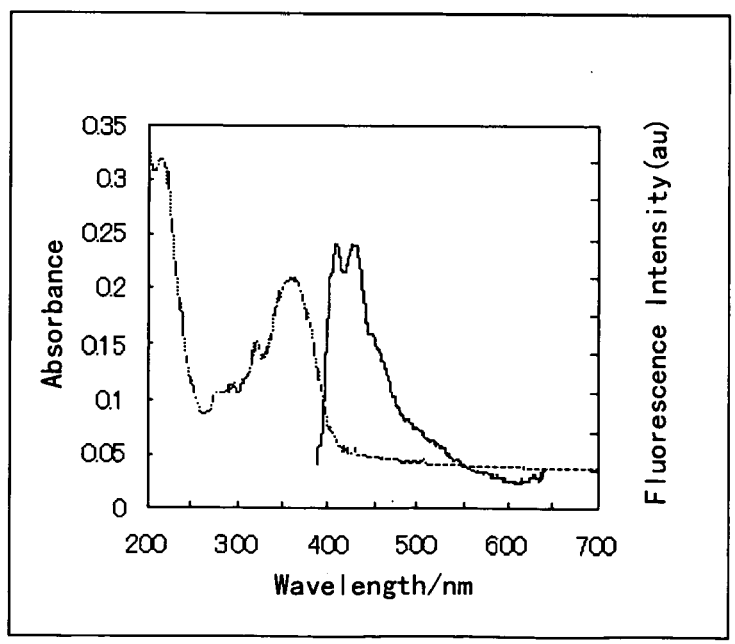

The present invention will be described in detail below.
The EL polymer of the present invention has repeating units represented by the following formula (1).

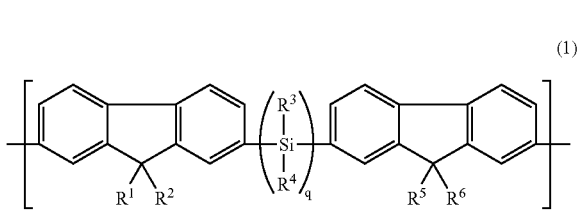

(1)

In formula (1), $R^1$, $R^2$, $R^5$ and $R^6$ each independently indicate a hydrogen atom or substituent group. Accordingly, $R^1$, $R^2$, $R^5$ and $R^6$ may be the same or different. Here, examples of substituent groups include linear, branched or ring-containing alkyl groups, e.g., t-butyl group, cyclohexyl group, 2-ethylhexyl group or n-octyl group; linear, branched or ring-containing alkenyl groups, e.g., propenyl group; linear, branched or ring-containing alkynyl groups, e.g., ethynyl group; aralkyl group, e.g., benzyl group; aryl groups, e.g., phenyl group, naphthyl group, anthryl group or pyranyl group; heteroaryl group in which elements other than carbon (nitrogen atom, sulfur atom and/or oxygen atom or the like) form a portion of the aromatic moiety, e.g., pyridyl group, thienyl group or carbazolyl group; alkoxy groups, e.g., methoxy group or isopropoxy group; aryloxy groups, e.g., phenoxy group or naphthoxy group; and aliphatic heterocyclic groups, e.g., piperidyl group or the like. In particular, phenyl group, naphthyl group, cyclohexyl group, 2-ethylhexyl group, n-octyl group or n-hexyl group are preferable as $R^1$, $R^2$, $R^5$ and $R^6$, and n-octyl group is especially preferable.

Furthermore, in formula (1), $R^3$ and $R^4$ each independently indicate an aryl group or alkyl group. Accordingly, $R^3$ and $R^4$ may be the same or different. Here, examples of aryl groups include phenyl group, p-tolyl group, mesityl group, 4-t-butylphenyl group, naphthyl group, anthryl group and the like, and examples of alkyl group include linear, branched or ring-containing alkyl groups, e.g., methyl group, ethyl group, t-butyl group and the like. In particular, methyl group, ethyl group, t-butyl group, p-tolyl group, mesityl group, 4-t-butylphenyl group, naphthyl group or anthryl group are preferable as $R^3$ and $R^4$, and methyl group or phenyl group is especially preferable.

Furthermore, q is 1 or 2, and X is halogen atom, especially bromine atom.

Accordingly, especially preferable concrete examples of the repeating unit represented by formula (1) in the electroluminescent polymer of the present invention are a repeating unit in which $R_1$, $R^2$, $R^5$ and $R^6$ are n-octyl groups, $R^3$ and $R^4$ are phenyl groups, and q is 1 (formula (4)); a repeating unit in which $R^1$, $R^2$, $R^5$ and $R^6$ are n-octyl groups, $R^3$ and $R^4$ are methyl groups, and q is 1 (formula (5)); a repeating unit in which $R^1$, $R^2$, $R^5$ and $R^6$ are n-octyl groups, $R^3$ and $R^4$ are methyl groups, and q is 2 (formula (6)); a repeating unit in which $R^1$, $R^2$, $R^5$ and $R^6$ are n-octyl groups, $R^3$ and $R^4$ are mesityl groups, and q is 1 (formula (7)); a repeating unit in which $R^1$, $R^2$, $R^5$ and $R^6$ are n-octyl groups, $R^3$ and $R^4$ are p-t-butylphenyl groups, and q is 1 (formula (8)) and the like.

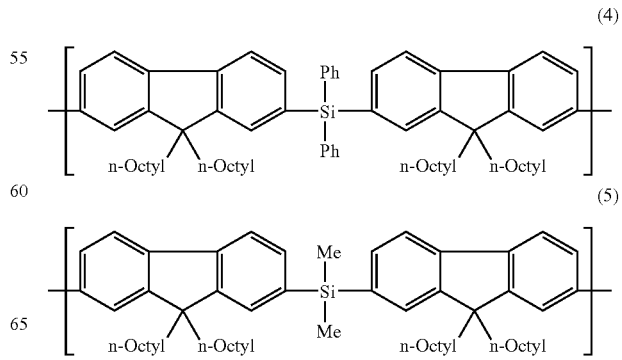

-continued

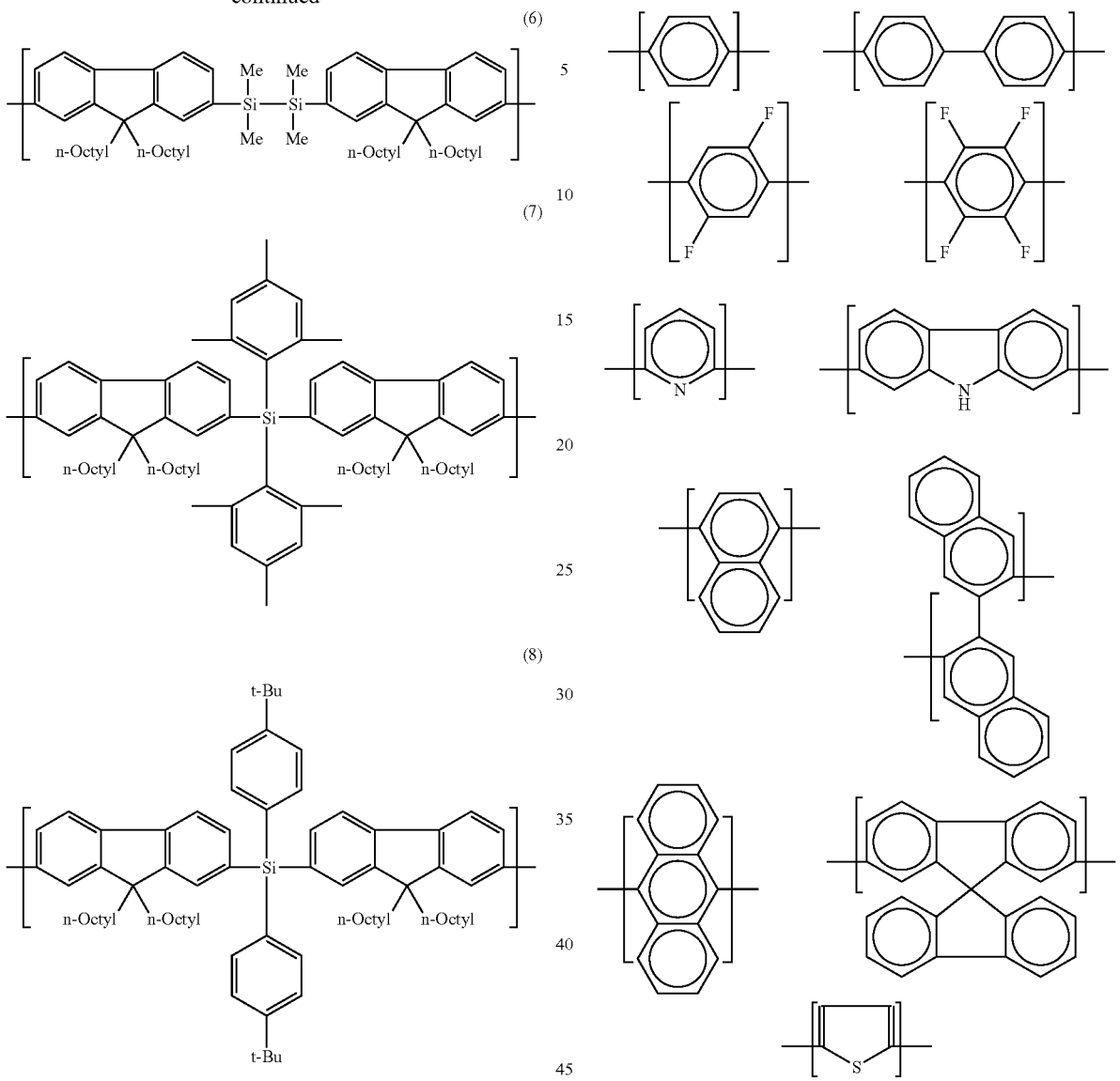

In the EL polymer of the present invention, if the content of the repeating unit represented by formula (1) is too small, blue light emission with a high color purity cannot be obtained. Accordingly, it is preferable that this content be 0.1 mol % or greater, and a content of 1 mol % or greater is even more preferable.

Furthermore, if the weight average molecular weight of the EL polymer of the present invention is too small, uniform film formation is difficult. On the other hand, if this weight average molecular weight is too large, purification is difficult, and solubility and solution stability are insufficient. Accordingly, this weight average molecular weight is preferably 1000 to 50,000,000, and is even more preferably 2000 to 500,000.

Furthermore, if necessary, in addition to the repeating unit represented by formula (1), the EL polymer of the present invention may contain the other repeating units shown below.

Preferably the EL polymer of the present invention may contain repeating units (fluorene units) represented by formula (2) (preferably at the rate of 10 to 99.9 mol %, and even more preferably at the rate of 50 to 99 mol %).

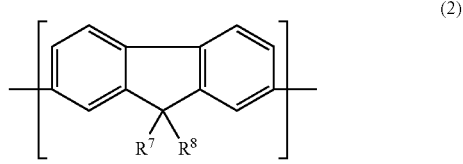

In formula (2), $R^7$ and $R^8$ each independently indicate a hydrogen atom or a substituent group. Accordingly, $R^7$ and $R^8$ may be the same or different. Here, examples of substituent groups include linear, branched or ring-containing alkyl groups, e.g., t-butyl group, cyclohexyl group, 2-ethylhexyl group or n-octyl group; linear, branched or ring-containing alkenyl groups, e.g., propenyl group; linear, branched or ring-containing alkynyl groups, e.g., ethynyl group; aralkyl groups, e.g., benzyl group; aryl groups, e.g., phenyl group, naphthyl group, anthryl group or pyranyl group; heteroaryl groups in which elements other than carbon (nitrogen atom, sulfur atom and/or oxygen atom or the like) form a portion of the aromatic moiety, e.g., pyridyl group, thienyl group or carbazolyl group; alkoxy groups, e.g., methoxy group or isopropoxy group; aryloxy groups, e.g., phenoxy group or naphthoxy group; and aliphatic heterocyclic groups, e.g., piperidyl group or the like. In particular, phenyl group, naphthyl group, cyclohexyl group, 2-ethylhexyl group, n-octyl group or n-hexyl group are preferable as $R^7$ and $R^8$ and n-octyl group is especially preferable.

The EL polymer of the present invention can be manufactured as follows.

Specifically, an alkyllithium (preferably n-butyllithium) is caused to act on 2,7-halogenofluorene derivatives (see manufacturing operation in Example 1 of Japanese Patent Publication No. 11-51535) represented by formula (9a) and formula (9b) (in formula (9a) and formula (9b), $R^1$, $R^2$, $R^5$ and $R^6$ are as defined in formula (1), and X is a halogen atom, preferably a bromine atom) in a solvent (ether, toluene or the like), preferably at a temperature of −20 to 20° C.

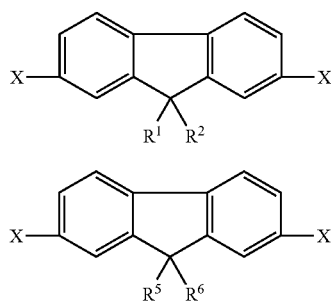

Then, in cases where a monosilane type compound such as those represented by formula (4) and formula (5) is to be manufactured, $(R^3R^4)_2SiY_2$ (here, $R^3$ and $R^4$ are as defined in formula (1), and Y is chlorine atom, bromine atom, iodine atom, methoxy group, ethoxy group or the like, preferably chlorine atom or methoxy group) is reacted in a molar amount that is approximately half the total amount of the compounds represented by formula (9a) and formula (9b), and in cases where a disilane type compound such as that represented by formula (6) is to be manufactured, $(R^3R^4)_4Si_2Y_2$ (here, $R^3$, $R^4$ and Y are as described above) is reacted in a molar amount that is approximately half the total amount of the compounds represented by formula (9a) and formula (9b), thus producing a bisfluorenylsilane compound represented by formula (3)

(3)

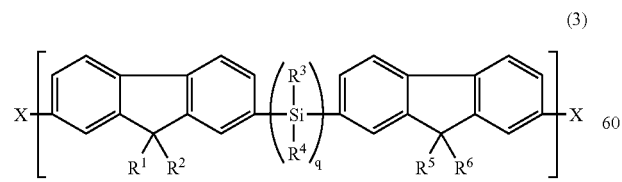

where in the formula, $R^1$, $R^2$, $R^3$, $R^4$, $R^5$, $R^6$ and q are as defined in formula (1), and X is as defined in formula (9a) and formula (9b), and this bisfluorenylsilane compound is used as an intermediate raw material. This intermediate raw material is a novel compound, and is extremely useful as a manufacturing raw material for the EL polymer of the present invention. Here, preferable examples of compounds represented by formula (3) include a compound in which $R^1$, $R^2$, $R^5$ and $R^6$ are n-octyl groups, $R^3$ and $R^4$ are phenyl groups, q is 1, and X is bromine atom (formula (10)); a compound in which $R^1$, $R^2$, $R^5$ and $R^6$ are n-octyl groups, $R^3$ and $R^4$ are methyl groups, q is 1, and X is bromine atom (formula (11)); a compound in which $R^1$, $R^2$, $R^5$ and $R^6$ are n-octyl groups, $R^3$ and $R^4$ are methyl groups, q is 2, and X is bromine atom (formula (12)); a compound in which $R^1$, $R^2$, $R^5$ and $R^6$ are n-octyl groups, $R^3$ and $R^4$ are mesityl groups, q is 1, and X is bromine atom (formula (13)); and a compound in which $R^1$, $R^2$, $R^5$ and $R^6$ are n-octyl groups, $R^3$ and $R^4$ are p-t-butylphenyl groups, q is 1, and X is bromine atom (formula (14)).

(10)

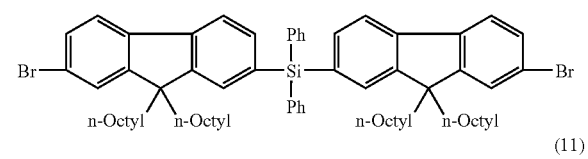

(11)

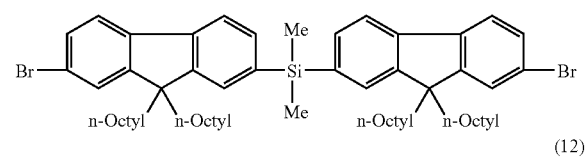

(12)

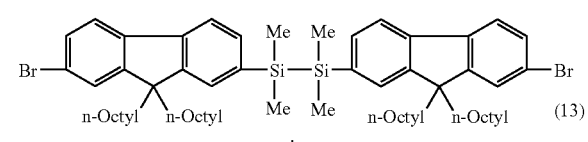

(13)

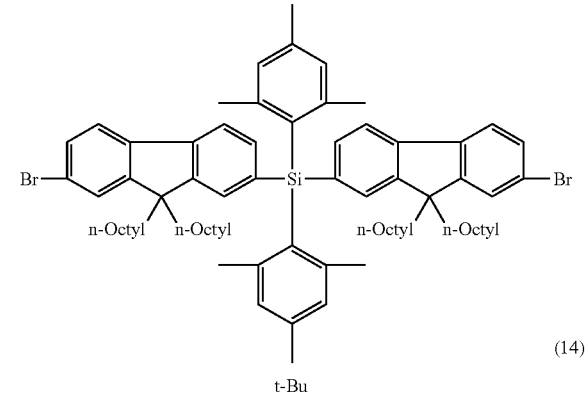

(14)

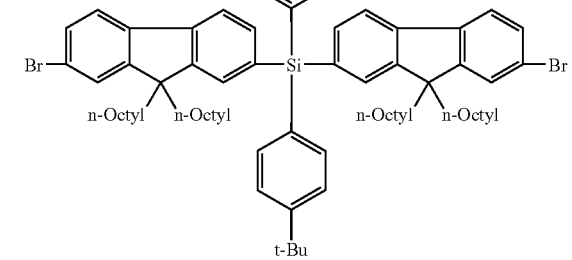

Next, an EL polymer with repeating units represented by formula (1) can be manufactured by reacting a fluorene compound in which a boron structure is introduced onto the 2 and 7 positions as represented by formula (15)

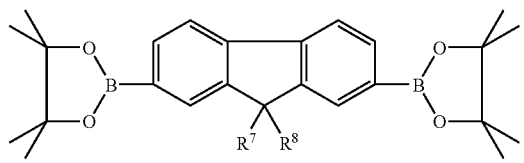

(15)

where in formula (15), $R^7$ and $R^8$ are as defined in formula (2)), and if necessary a fluorene compound represented by formula (2), with the bisfluorenylsilane compound represented by formula (3), in the presence of a palladium catalyst (e.g., Pd(PPh$_3$)$_4$) and an alkali carbonate (e.g., potassium carbonate) in a solvent (e.g., toluene, THF, water or the like) at a temperature of 0 to 100° C. Furthermore, the compound represented by formula (15) can be manufactured by reacting 2-isopropoxy-4,4,5,5-tetramethyl-1,3,2-dioxaborolane with the compound represented by formula (2) in the presence of an alkyllithium (e.g., n-butyllithium) in a solvent (e.g., hexane or THF) at a low temperature (e.g., −78° C.) (see N. Miyaura and A. Suzuki, Chem. Rev., 1995, 95, 2457).

A film of the EL polymer of the present invention can be utilized as an organic EL element by clamping this film as a light-emitting layer between a pair of electrodes. The basic layer construction of this organic EL element can be formed in the same manner as that of a universally known organic EL element.

EXAMPLES

The present invention will be concretely described below in terms of examples.

Reference Example 1

(Synthesis of 2,7-Dibromo-9,9-dioctylfluorene)

10.0 g (31.0 mmol) of 2,7-dibromofluorene, 19.7 g (89.0 mmol) of 1-bromooctane, 25 ml of dimethylsulfoxide, 24.9 g (623 mmol) of sodiumhydroxide and 50 ml of water were added to a 200 ml three-necked flask equipped with a reflux condenser, and this mixture was heated to 80° C. After the dissolution of the 2,7-dibromofluorene was confirmed, 608 mg (2.66 mmol) of benzyltriethylammonium chloride was added, and the resulting mixture was heated and agitated for 20 hours.

The reaction solution thus obtained was extracted with hexane; afterward, the extract was dried and the hexane was distilled away. Then, the excess 1-bromooctane was distilled away under heating and reduced pressure. Next, the residue thus obtained was purified by column chromatography (carrier: silica gel, eluent: hexane), thus isolating 2,7-dibromo-9,9-dioctylfluorene as colorless crystals (amount yielded: 14.31 g (26.1 mmol), yield: 84.1%). Furthermore, the identification of the compound thus obtained was accomplished by MS, $^1$H NMR and $^{13}$C NMR.

Reference Example 2

(Synthesis of Fluorene Compound Represented by Formula (15) with Boron Structure Introduced onto 2 and 7 Positions ($R^1$=n-Octyl group))

Under a nitrogen gas atmosphere, 8.20 g (15.0 mmol) of 2,7-dibromo-9,9-dioctylfluorene and 100 ml of tetrahydrofuran were added to a 200 ml three-necked flask equipped with a 100 ml dropping funnel and a reflux condenser. After the reaction vessel was cooled to −78° C. using a methanol-dry ice bath, 28.0 ml (44.2 mmol) of n-butyllithium (1.58 M hexane solution) was added dropwise via the dropping funnel. Following agitation for approximately 1 hour with the temperature maintained at −78° C., 9.0 ml (44 mmol) of 2-isopropoxy-4,4,5,5-tetramethyl-1,3,2-dioxaborolane was added, the methanol—dry ice bath was removed, and the mixture was agitated for approximately 11 hours.

The reaction solution thus obtained was extracted with diethyl ether. Then, the colorless crystals that were obtained after the extract was dried and the diethyl ether was distilled away were washed with methanol and purified, thus producing the fluorene compound represented by formula (15) ($R^1$=n-octyl group) in the form of colorless crystals (amount yielded: 7.94 g (12.4 mmol), yield: 83.2%). Furthermore, the identification of the compound thus obtained was accomplished by $^1$H NMR and $^{13}$C NMR.

Example 1

Synthesis of Bisfluorenyldiphenylsilane

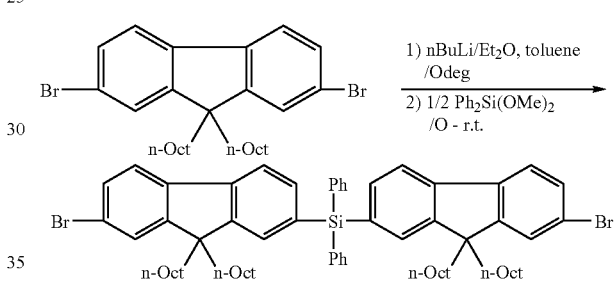

Under a nitrogen gas atmosphere, 4.90 g (8.94 mmol) of 2,7-dibromo-9,9-dioctylfluorene, 20 ml of diethyl ether and 10 ml of toluene were added to a 100 ml three-necked flask equipped with a reflux condenser and a dropping funnel. Under cooling by an ice bath, 6.1 ml (9.76 mmol) of a hexane solution of n-butyllithium (1.6 M) was added dropwise. As the hexane solution of butyllithium was added dropwise, the solution turned red. The solution was agitated "as is" for approximately 1 hour; then, 1.03 g (4.21 mmol) of dimethoxydiphenylsilane was added, and this mixture was reacted under agitation all night.

Following the completion of the reaction, the reaction solution was subjected to an extraction treatment; the extract thus obtained was dried and concentrated, and the low-molecular components were removed from the concentrate by Kugelrohr vacuum distillation (200° C./0.1 mmHg). Then, a component in which Rf=0.71 was separated from the distillation residue by column chromatography (carrier: silica gel, eluent: hexane:toluene 6:1), and the bisfluorenyldiphenylsilane represented by formula (10) was isolated as a colorless viscous substance showing fluorescence (amount yielded: 2.77 g, yield: 60.9%). The identification data of the compound thus obtained were as follows:

$^1$H NMR (CDCl$_3$, δ): 7.67–7.14 (m, 22H), 1.90 (t, J=7.5 Hz, 8H), 1.22–1.03 (m, 40H), 0.82 (t, J=6.9 Hz, 12H), 0.61 (brs, 8H)

$^{13}$C NMR (CDCl$_3$, δ): 153.2, 149.3, 141.4, 139.7, 136.2, 135.1, 134.7, 132.9, 130.7, 129.9, 129.5, 127.8, 126.1, 121.4, 121.3, 119.3, 55.4, 40.2, 31.9, 30.1, 29.40, 29.37, 24.0, 22.7, 14.2.

$^{29}$Si NMR (CDCl$_3$, δ): −13.3.
FAB-MS: 1116 (M$^+$)
Elemental analysis:
Theoretical values: C 75.1%, H 8.1% (for C$_{70}$H$_{90}$Br$_2$Si)
Experimental values: C 75.5%, H 8.1%

Example 2

Synthesis of Bisfluorenyldimethylsilane

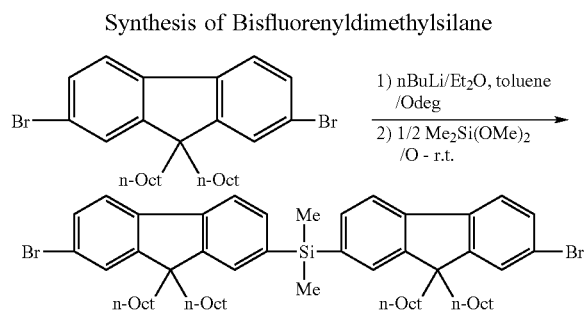

Under a nitrogen gas atmosphere, 5.00 g (9.11 mmol) of 2,7-dibromo-9,9-dioctylfluorene, 20 ml of diethyl ether and 10 ml of toluene were added to a 100 ml three-necked flask equipped with a reflux condenser and a dropping funnel. Under cooling by an ice bath, 6.2 ml (9.92 mmol) of a hexane solution of n-butyllithium (1.6 M) was added dropwise. As the butyllithium was added, the solution turned red. This solution was agitated "as is" for approximately 1 hour; then, 520 mg (4.33 mmol) of dimethoxydimethylsilane was added, and the resulting mixture was agitated and reacted all night.

Following the completion of the reaction, the reaction solution was subjected to an extraction treatment. The extract thus obtained was dried and concentrated, and low-molecular components were removed from the concentrate by Kugelrohr vacuum distillation (200° C./0.1 mmHg). Next, a component in which Rf=0.75 was separated from the distillation residue by column chromatography (carrier: silica gel, eluent: hexane:toluene=7:1), and the bisfluorenyldimethylsilane represented by formula (11) was isolated as a colorless viscous substance showing fluorescence (amount yielded: 3.20 g, yield: 75.0%). The identification data of the compound thus obtained were as follows:

$^1$H NMR (CDCl$_3$, δ): 7.67–7.14 (m, 12H), 1.93 (brs, 8H), 1.23–1.05 (m, 40H), 0.823 (t, J=6.9 Hz, 12H), 0.62 (brs, 14H).
$^{13}$C NMR (CDCl$_3$, δ): 153.0, 149.3, 140.8, 139.9, 137.3, 132.9, 129.8, 128.3, 126.1, 121.12, 121.07, 119.0, 55.4, 40.1, 31.9, 30.0, 29.28, 29.25, 23.8, 22.7, 14.2, −1.68.
$^{29}$Si NMR (CDCl$_3$, δ): −7.08.
FAB-MS: 992 (M$^+$)
Elemental analysis:
Theoretical values: C 72.4%, H 8.7% (for C$_{60}$H$_{86}$Br$_2$Si)
Experimental values: C 73.3%, H 8.9%

Example 3

Synthesis of 1,2-Bisfluorenyltetramethyldisilane

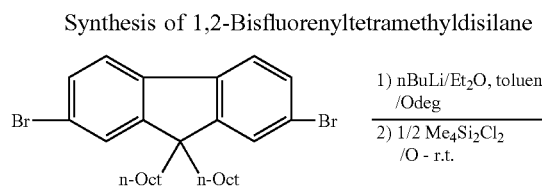

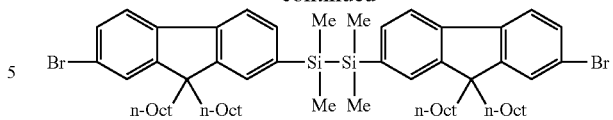

Under a nitrogen gas atmosphere, 4.99 g (9.10 mmol) of 2,7-dibromo-9,9-dioctylfluorene, 20 ml of diethyl ether and 10 ml of toluene were added to a 100 ml three-necked flask equipped with a reflux condenser and a dropping funnel. Under cooling by an ice bath, 6.2 ml (9.92 mmol) of a hexane solution of n-butyllithium (1.6 M) was added dropwise. As the butyllithium was added dropwise, the solution turned red. This solution was agitated "as is" for approximately 1 hour; then, 810 mg (4.33 mmol) of 1,2-dichlorotetramethyldisilane was added, and the resulting mixture was agitated and reacted all night.

Following the completion of the reaction, the reaction solution was subjected to an extraction treatment. The extract thus obtained was dried and concentrated, and low-molecular components were removed from the concentrate by Kugelrohr vacuum distillation (200° C./0.1 mmHg). Next, a component in which Rf=0.73 was separated from the distillation residue by column chromatography (carrier: silica gel, eluent: hexane:toluene=7:1), and the 1,2-bisfluorenyltetramethyldisilane represented by formula (12) was isolated as a colorless viscous substance showing fluorescence (amount yielded: 2.04 g, yield: 46.8%). The identification data of the compound thus obtained were as follows:

$^1$H NMR (CDCl$_3$, δ): 7.68–7.31 (m, 12H), 1.93 (t, J=7.5 Hz, 8H), 1.27–0.93 (m, 0H), 0.826 (t, J=6.9 Hz, 12H), 0.64 (brs, 8H), 0.37 (s, 12H).
$^{13}$C NMR (CDCl$_3$, δ): 152.8, 149.3, 140.3, 140.0, 138.1, 132.2, 129.8, 127.9, 126.1, 121.1, 121.0, 119.0, 55.3, 40.3, 31.9, 30.1, 29.4, 29.3, 23.8, 22.7, 14.2, −3.8.
$^{29}$Si NMR (CDCl$_3$, δ): −21.3.
FAB-MS: 1050 (M$^+$)
Elemental analysis:
Theoretical values: C 70.7%, H 8.8% (for C$_{62}$H$_{92}$Br$_2$Si$_2$)
Experimental values: C 71.3%, H 8.9%

Example 4

Synthesis of Bisfluorenyl-di(t-butylphenyl)silane

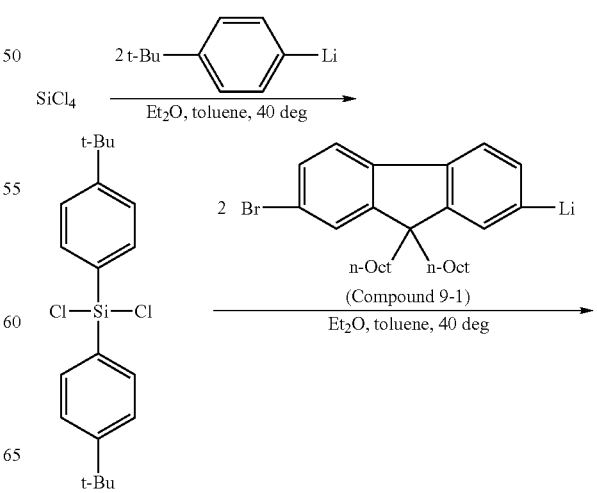

-continued

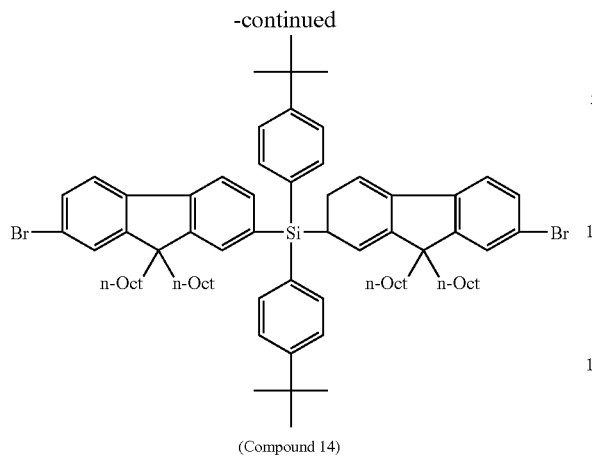

(Compound 14)

Under a nitrogen gas atmosphere, 1.16 g (6.82 mmol) of silicon tetrachloride, 10 ml of diethyl ether and 15 ml of toluene were added to a 100 ml three-necked flask equipped with a reflux condenser and a dropping funnel. A separately prepared diethyl ether solution (15 ml) of 4-t-butylphenyllithium (14.7 mmol) was added dropwise to this mixture, and the resulting mixture was reacted for approximately 72 hours at 40° C. Furthermore, a separately prepared diethyl ether (25 ml)—toluene (15 ml) mixed solution of 2-bromo-7-lithio-9,9-dioctylfluorene (compound 9-1) (14.5 mmol) was added dropwise, and the resulting mixture was reacted for approximately 72 hours at 40° C. An extraction was performed from diethyl ether, and the extract was dried and concentrated. Afterward, low-molecular components were removed by Kugelrohr vacuum distillation (200° C./0.1 mmHg). Next, a component in which Rf=0.80 was separated from the distillation residue by column chromatography (carrier: silica gel, eluent: hexane:toluene=3:1), and compound 14 was isolated as a slightly yellowish viscous substance showing fluorescence. The amount yielded as 4.89 g (3.97 mmol), and the yield was 58.2%. The identification data of the compound thus obtained were as follows:

$^1$H NMR (CDCl$_3$, δ): 7.65–7.34 (m, 20H), 1.90 (brs, 8H), 1.32 (s, 18H), 1.28–0.83 (m, 40H), 0.83 (t, J=6.9 Hz, 12H), 0.62 (brs, 8H).

$^{13}$C NMR (CDCl$_3$, δ): 153.7, 152.3, 149.1, 141.2, 139.9, 136.0, 135.2, 133.5, 131.3, 130.7, 128.1, 126.1, 124.7, 121.3, 121.2, 119.2, 55.4, 40.3, 34.7, 31.9, 31.3, 30.2, 29.50, 29.46, 24.0, 22.8, 14.2.

$^{29}$Si NMR (CDCl$_3$, δ): −13.9.

FAB-MS: 1228 (M$^+$)

Elemental analysis:

Theoretical values: C 76.1%, H 8.6% (for C$_{78}$H$_{106}$Br$_2$Si)

Experimental values: C 76.4%, H 8.6%

Example 5

Synthesis of Bisfluorenyldimesitylsilane

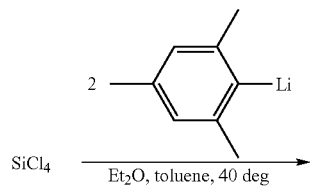

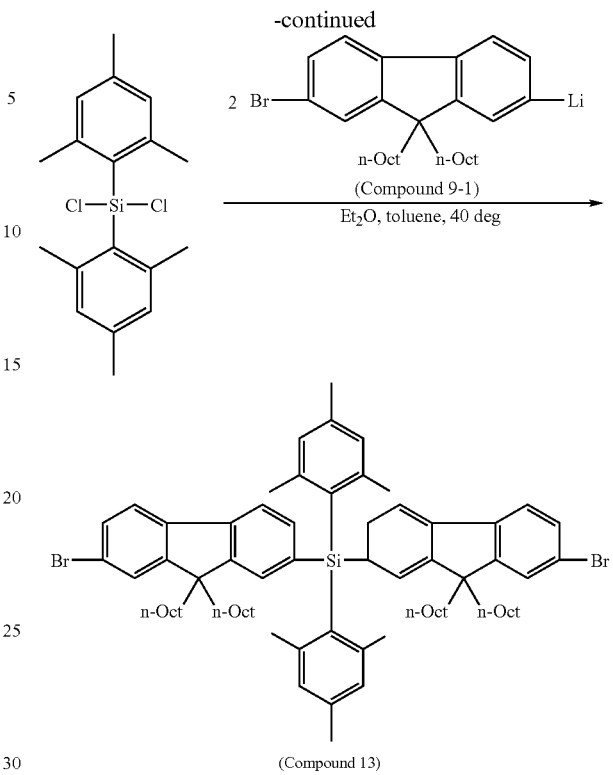

(Compound 13)

Under a nitrogen gas atmosphere, 1.19 g (7.00 mmol) of silicon tetrachloride, 10 ml of diethyl ether and 10 ml of toluene were added to a 100 ml three-necked flask equipped with a reflux condenser and a dropping funnel. A separately prepared diethyl ether solution (15 ml) of mesityllithium (14.6 mmol) was added dropwise to this mixture, and the resulting mixture was reacted for approximately 72 hours at 40° C. Furthermore, a separately prepared diethyl ether (25 ml)—toluene (15 ml) solution of 2-bromo-7-lithio-9,9-dioctylfluorene (compound 9-1) (14.5 mmol) was added dropwise, and the resulting mixture was reacted for approximately 72 hours at 40° C. An extraction was performed from diethyl ether, and the extract was dried and concentrated. Afterward, low-molecular components were removed by Kugelrohr vacuum distillation (200° C./0.1 mmHg). Next, a component in which Rf=0.82 was separated from the distillation residue by column chromatography (carrier: silica gel, eluent: hexane:toluene=3:1), and compound 13 was isolated as a slightly yellowish viscous substance showing fluorescence. The amount yielded was 2.42 g (2.01 mmol), and the yield rate was 28.7%. The identification data of the compound thus obtained were as follows:

$^1$H NMR (CDCl$_3$, δ): 7.70–7.40 (m, 12H), 6.83 (s, 4H), 2.34 (s, 12H), 2.26 (s, 6H), 1.91 (brs, 8H), 1.25–0.90 (m, 40H), 0.82 (t, J=6.9 Hz, 12H), 0.60 (brs, 8H)

$^{13}$C NMR (CDCl$_3$, δ): 153.0, 149.3, 146.0, 144.3, 140.9, 139.8, 136.5, 134.5, 130.3, 129.8, 129.4, 192.1, 126.1, 121.3, 121.1, 119.2, 55.5, 40.3, 31.9, 30.1, 29.4, 29.3, 26.1, 24.0, 22.8, 21.2, 14.2.

$^{29}$Si NMR (CDCl$_3$, δ): −16.7.

FAB-MS: 1081 (M$^+$-Mes)

Elemental analysis:

Theoretical values: C 75.9%, H 8.5% (for C$_{76}$H$_{102}$Br$_2$Si)

Experimental values: C 75.3%, H 8.7%

Example 6

Synthesis of Fluorene Polymer (SiPh Monomer Content 10%)

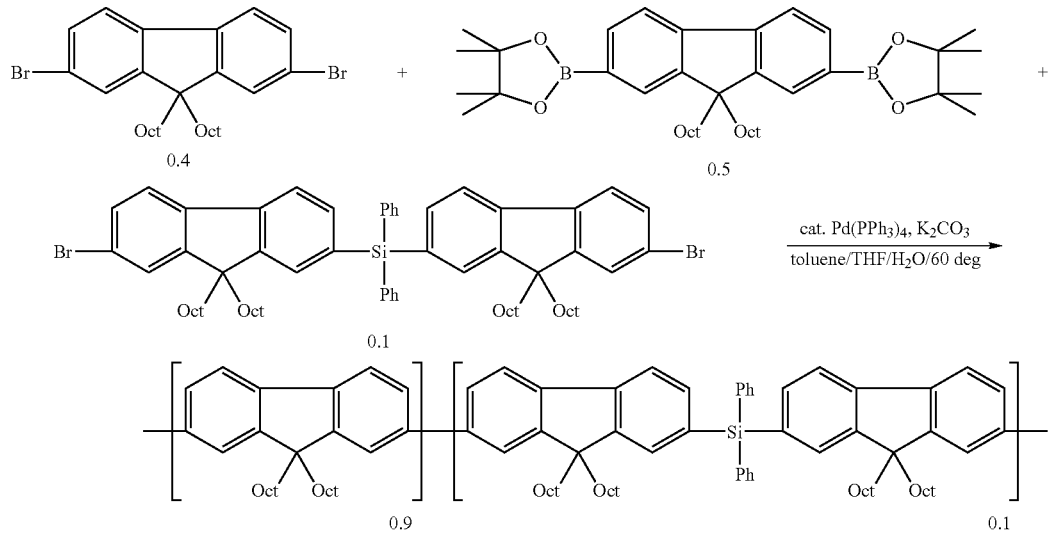

Under a nitrogen gas atmosphere, 518 mg (0.463 mmol) of bis(7-bromo-9,9-dioctylfluorenyl)diphenylsilane, 1.55 g (2.41 mmol) of 9,9-dioctylfluorene with boron structures introduced onto the 2 and 7 positions, 1.06 g (1.93 mmol) of 2,7-dibromofluorene, 2.26 g (16.4 mmol) of potassium carbonate, 15 ml of THF and 8 ml of distilled water were added to a 100 ml three-necked flask equipped with a reflux condenser, and this mixture was heated to 60° C. After the dissolution of the substrate was confirmed, one full spatula of tetrakis(triphenylphosphine)palladium was added, and the mixture was heated and agitated for approximately 48 hours. 5 ml of toluene was further added, and the mixture was heated and refluxed for approximately 24 hours. When toluene was added following cooling and the solvent was distilled away as far as possible, a high-viscosity substance was obtained.

The substance thus obtained was washed with 1 N hydrochloric acid, a 1 N aqueous solution of sodium hydroxide and distilled water in that order, so that the potassium carbonate was removed. Furthermore, dissolution in a small amount of warm THF and re-precipitation from methanol was performed twice, and the product was purified by performing a Soxhlet extraction (acetone) for approximately 48 hours, thus producing an EL polymer containing repeating units represented by formula (4) (bisfluorenyldiphenylsilane) at the rate of 10 mol % and fluorene units represented by formula (2) at the rate of 90 mol % (amount yielded: 1.22 g). As a result of GPC (eluent: THF, according to comparison with a standard polystyrene of known molecular weight), this polymer showed an Mw value (weight average molecular weight) of 34,686 and an Mn value (number average molecular weight) of 14,181. Furthermore, the concentration of inorganic metallic elements in this polymer was less than the detection limit (0.1%) of EDX (energy distribution type fluorescent X-ray measurement).

Example 7

Synthesis of Fluorene Polymer (SiPh Monomer Content 25%)

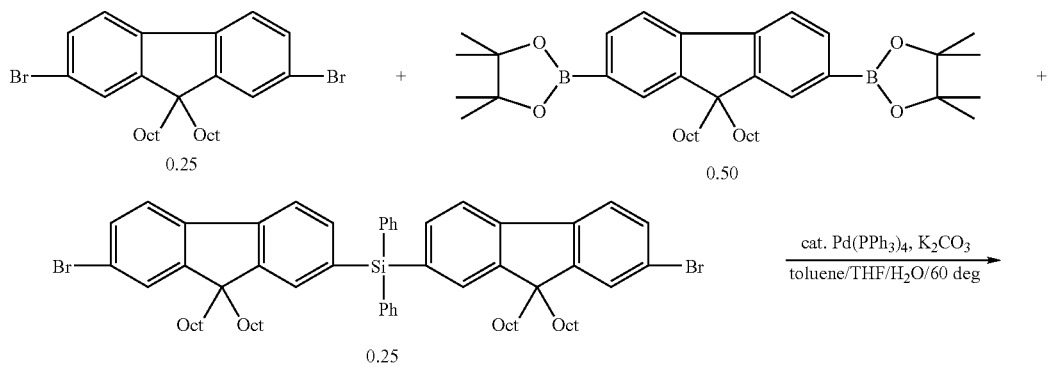

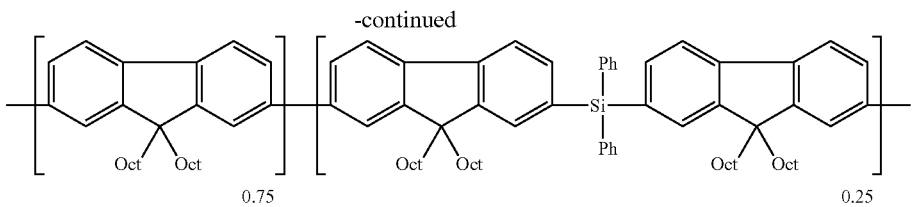

Under a nitrogen gas atmosphere, 1.28 g (1.14 mmol) of bis(7-bromo-9,9-dioctylfluorenyl)diphenylsilane, 1.51 g (2.35 mmol) of 9,9-dioctylfluorene with boron structures introduced onto the 2 and 7 positions, 648 mg (1.17 mmol) of 2,7-dibromofluorene, 2.20 g (15.9 mmol) of potassium carbonate, 15 mol of THF and 8 ml of distilled water were added to a 100 ml three-necked flask equipped with a reflux condenser, and this mixture was heated to 60° C. After the dissolution of the substrate was confirmed, one full spatula of tetrakis(triphenylphosphine)palladium was added, and the mixture was heated and agitated for approximately 48 hours. 5 ml of toluene was further added, and the mixture was heated and refluxed for approximately 24 hours. When toluene was added following cooling and the solvent was distilled away as far as possible, a high-viscosity substance was obtained.

The substance thus obtained was washed with 1 N hydrochloric acid, a 1 N aqueous solution of sodium hydroxide and distilled water in that order, so that the potassium carbonate was removed. Furthermore, dissolution in a small amount of warm THF and re-precipitation from methanol was performed twice, and the product was purified by performing a Soxhlet extraction (acetone) for approximately 48 hours, thus producing an EL polymer containing repeating units represented by formula (4) (bisfluorenyldiphenylsilane) at the rate of 25 mol % and fluorene units represented by formula (2) at the rate of 75 mol % (amount yielded: 958 mg). As a result of GPC (eluent: THF, according to comparison with a standard polystyrene of known molecular weight), this polymer showed an Mw value (weight average molecular weight) of 13,667 and an Mn value (number average molecular weight) of 8,979. Furthermore, the concentration of inorganic metallic elements in this polymer was less than the detection limit (0.1%) of EDX (energy distribution type fluorescent X-ray measurement).

Example 8

Synthesis of Fluorene Polymer (—Si(Ph)$_2$ Monomer Content 50%)

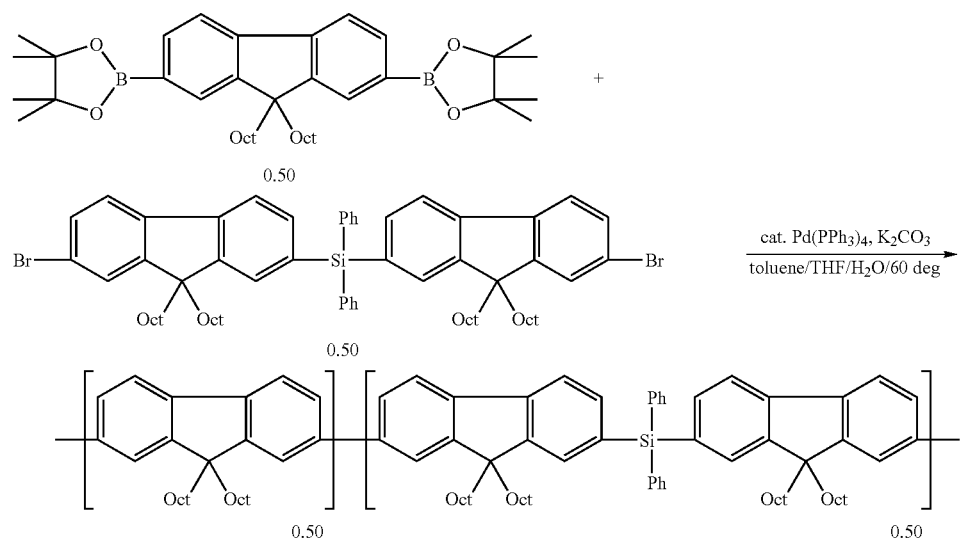

Under a nitrogen gas atmosphere, 998 mg (0.892 mmol) of bis(7-bromo-9,9-dioctylfluorenyl)diphenylsilane, 586 mg (0.911 mmol) of 9,9-dioctylfluorene with boron structures introduced onto the 2 and 7 positions, 2.24 g (16.2 mmol) of potassium carbonate, 15 ml of THF and 8 ml of distilled water were added to a 100 ml three-necked flask equipped with a reflux condenser, and this mixture was heated to 60° C. After the dissolution of the substrate was confirmed, one full spatula of tetrakis(triphenylphosphine)palladium was added, and the mixture was heated and agitated for approximately 48 hours. 5 ml of toluene was further added, and the mixture was heated and refluxed for approximately 24 hours. When toluene was added following cooling and the solvent was distilled away as far as possible, a high-viscosity substance was obtained.

The substance thus obtained was washed with 1 N hydrochloric acid, a 1 N aqueous solution of sodium hydroxide and distilled water in that order, so that the potassium carbonate was removed. Furthermore, dissolution in a small amount of warm THF and re-precipitation from methanol was performed twice, and the product was purified by performing a Soxhlet extraction (acetone) for approximately 48 hours, thus producing an EL polymer containing repeating units represented by formula (4) (bisfluorenyldiphenylsilane) at the rate of 50 mol % and fluorene units represented by formula (2) at the rate of 50 mol % (amount yielded: 1.04 g). As a result of GPC (eluent: THF, according to comparison with a standard polystyrene of known molecular weight), this polymer showed an Mw value (weight average molecular weight) of 13,214 and an Mn value (number average molecular weight) of 5,108. Furthermore, the concentration of inorganic metallic elements in this polymer was less than the detection limit (0.1%) of EDX (energy distribution type fluorescent X-ray measurement).

Example 9

Synthesis of Fluorene Polymer (—Si(Me)$_2$ Monomer Content 25%)

hours. 5 ml of toluene was further added, and the mixture was heated and refluxed for approximately 24 hours. When toluene was added following cooling and the solvent was distilled away as far as possible, a high-viscosity substance was obtained.

The substance thus obtained was washed with 1 N hydrochloric acid, a 1 N aqueous solution of sodium hydroxide and distilled water in that order, so that the potassium carbonate was removed. Furthermore, dissolution in a small amount of warm THF and re-precipitation from methanol was performed twice, and the product was purified by performing a Soxhlet extraction (acetone) for approximately 48 hours, thus producing an EL polymer containing repeating units represented by formula (5) (bisfluorenyldimethylsilane) at the rate of 25 mol % and fluorene units represented by formula (2) at the rate of 75 mol % (amount yielded: 403 mg). As a result of GPC (eluent: THF, according to comparison with a standard polystyrene of known molecular weight), this polymer showed an Mw value (weight average

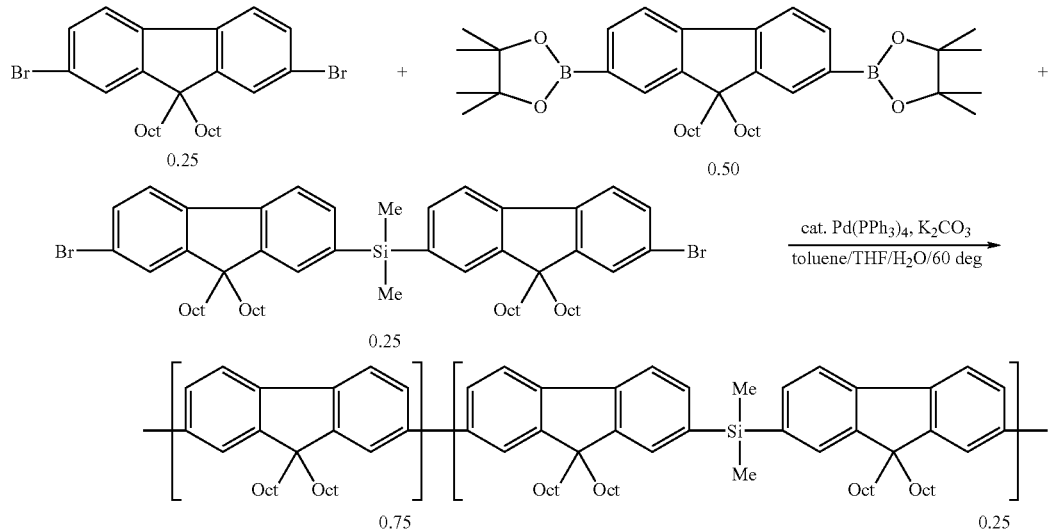

Under a nitrogen gas atmosphere, 990 mg (0.99 mmol) of bis(7-bromo-9,9-dioctylfluorenyl)dimethylsilane, 1.35 g (2.10 mmol) of 9,9-dioctylfluorene with boron structures introduced onto the 2 and 7 positions, 636 mg (1.16 mmol) of 2,7-dibromofluorene, 2.20 g (15.9 mmol) of potassium carbonate, 15 ml of THF and 8 ml of distilled water were added to a 100 ml three-necked flask equipped with a reflux condenser, and this mixture was heated to 60° C. After the dissolution of the substrate was confirmed, one full spatula of tetrakis(triphenylphosphine)palladium was added, and the mixture was heated and agitated for approximately 48 molecular weight) of 23,273 and an Mn value (number average molecular weight) of 9,767. Furthermore, the concentration of inorganic metallic elements in this polymer was less than the detection limit (0.1%) of EDX (energy distribution type fluorescent X-ray measurement).

Example 10

Synthesis of Fluorene Polymer (—Si(t-BuPh)$_2$ Monomer Content: 10%)

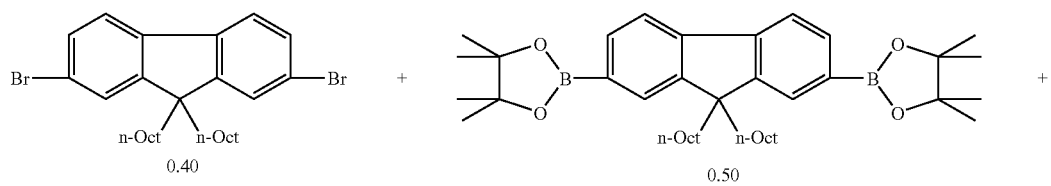

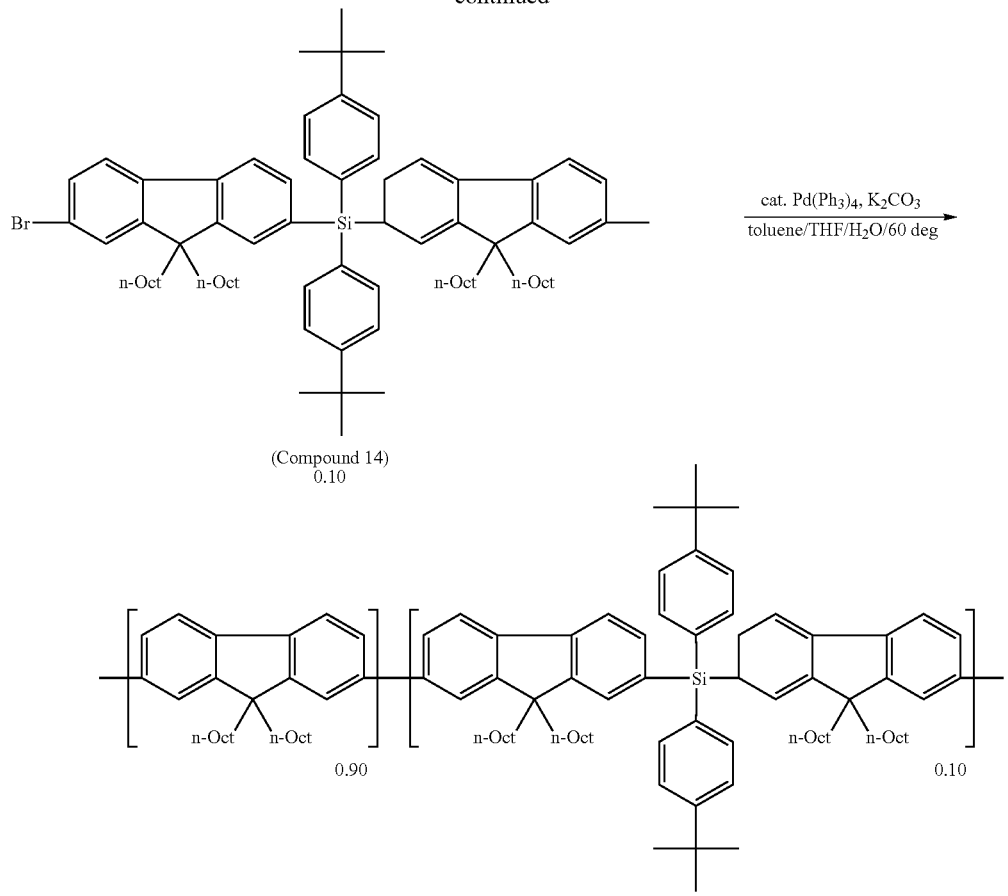

(Compound 14)
0.10

Under a nitrogen gas atmosphere, 289 mg (0.235 mmol) of butylphenylsilane (compound 14), 750 mg (1.17 mmol) of 9,9-dioctylfluorene with boron structures introduced onto the 2 and 7 positions, 515 mg (0.935 mmol) of 2,7-dibromo-9,9-dioctylfluorene, 2.22 g (16.1 mmol) of potassium carbonate, 15 ml of THF and 8 ml of distilled water were added to a 100 ml three-necked flask equipped with a reflux condenser, and this mixture was heated to 60° C. After the dissolution of the substrate was confirmed, one full spatula of tetrakis(triphenylphosphine)palladium was added, and the mixture was heated and agitated for approximately 48 hours. When toluene was added following cooling and the solvent was distilled away as far as possible, a high-viscosity substance was obtained.

The substance thus obtained was washed with 1 N hydrochloric acid, a 1 N aqueous solution of sodium hydroxide and distilled water in that order, so that the potassium carbonate was removed. Furthermore, dissolution in a small amount of warm THF and re-precipitation from methanol was performed twice, and the product was purified by performing a Soxhlet extraction (acetone) for approximately 48 hours, thus producing an EL polymer containing repeating units represented by formula (8) (bisfluorenyldi-t-butylphenylsilane) at the rate of 10 mol % and fluorene units represented by formula (2) at the rate of 90 mol % (amount yielded: 464 mg). As a result of GPC (eluent: THF, according to comparison with a standard polystyrene of known molecular weight), this polymer showed an Mw value (weight average molecular weight) of 27,671 and an Mn value (number average molecular weight) of 11,185. Furthermore, the concentration of inorganic metallic elements in this polymer was less than the detection limit (0.1%) of EDX (energy distribution type fluorescent X-ray measurement).

Example 11

Synthesis of Fluorene Polymer (—Si(t-BuPh)$_2$ Monomer Content: 25%)

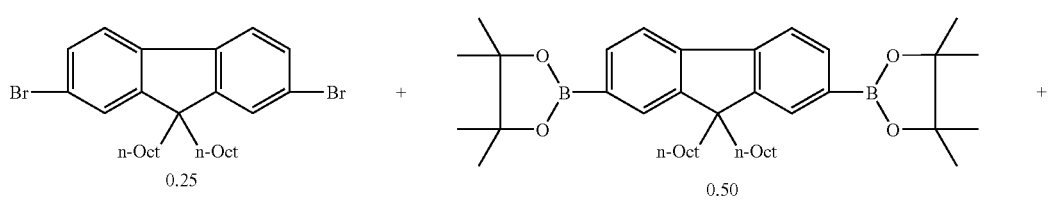

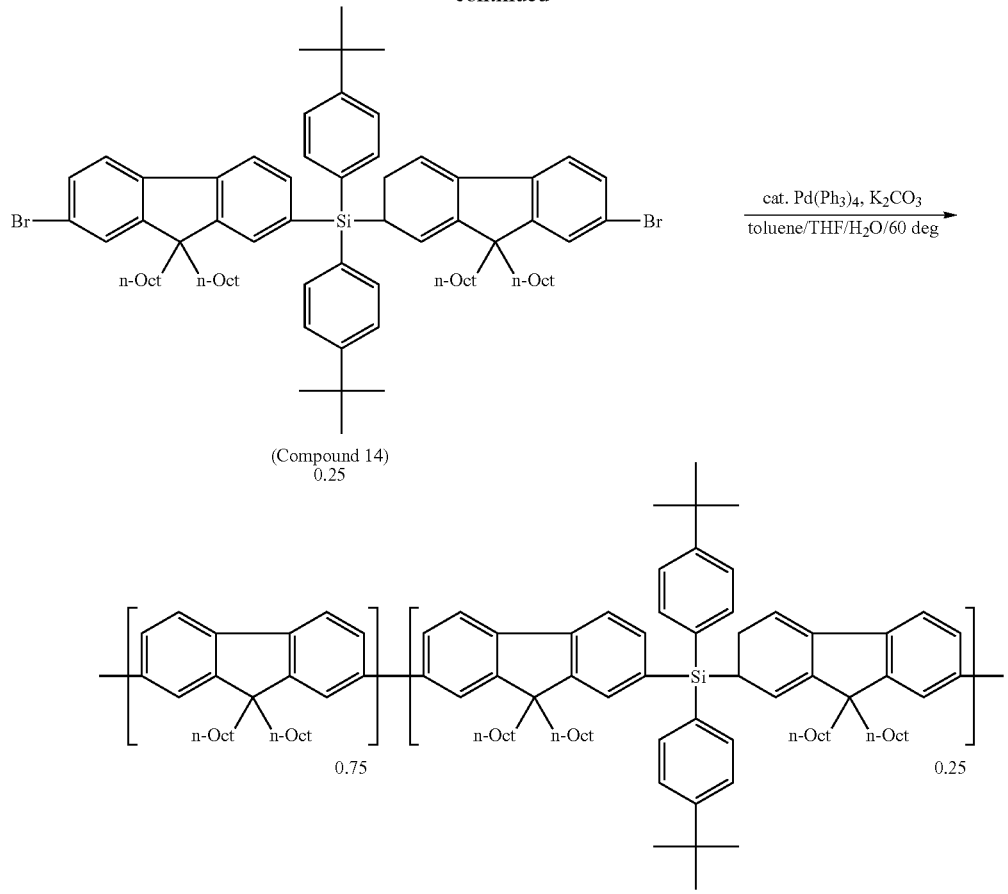

(Compound 14)
0.25

0.75   0.25

Under a nitrogen gas atmosphere, 720 mg (0.585 mmol) of bis(7-bromo-9,9-dioctylfluorenyl)di-t-butylphenylsilane (compound 14), 750 mg (1.17 mmol) of 9,9-dioctylfluorene with boron structures introduced onto the 2 and 7 positions, 321 mg (0.585 mmol) of 2,7-dibromo-9,9-dioctylfluorene, 2.20 g (15.9 mmol) of potassium carbonate, 15 ml of THF and 8 ml of distilled water were added to a 100 ml three-necked flask equipped with a reflux condenser, and this mixture was heated to 60° C. After the dissolution of the substrate was confirmed, one full spatula of tetrakis(triphenylphosphine)palladium was added, and the mixture was heated and agitated for approximately 48 hours. When toluene was added following cooling and the solvent was distilled away as far as possible, a high-viscosity substance was obtained.

The substance thus obtained was washed with 1 N hydrochloric acid, a 1 N aqueous solution of sodium hydroxide and distilled water in that order, so that the potassium carbonate was removed. Furthermore, dissolution in a small amount of warm THF and re-precipitation from methanol was performed twice, and the product was purified by performing a Soxhlet extraction (acetone) for approximately 48 hours, thus producing an EL polymer containing repeating units represented by formula (8) (bisfluorenyldi-t-butylphenylsilane) at the rate of 25 mol % and fluorene units represented by formula (2) at the rate of 75 mol % (amount yielded: 454 mg). As a result of GPC (eluent: THF, according to comparison with a standard polystyrene of known molecular weight), this polymer showed an Mw value (weight average molecular weight) of 27,340 and an Mn value (number average molecular weight) of 9,530. Furthermore, the concentration of inorganic metallic elements in this polymer was less than the detection limit (0.1%) of EDX (energy distribution type fluorescent X-ray measurement).

Example 12

Synthesis of Fluorene Polymer (—Si(Mes)$_2$ Monomer Content 25%)

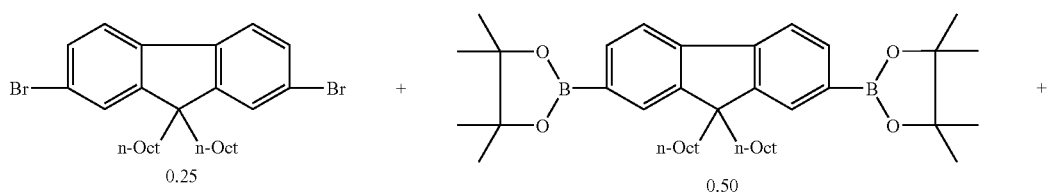

0.25   0.50

-continued

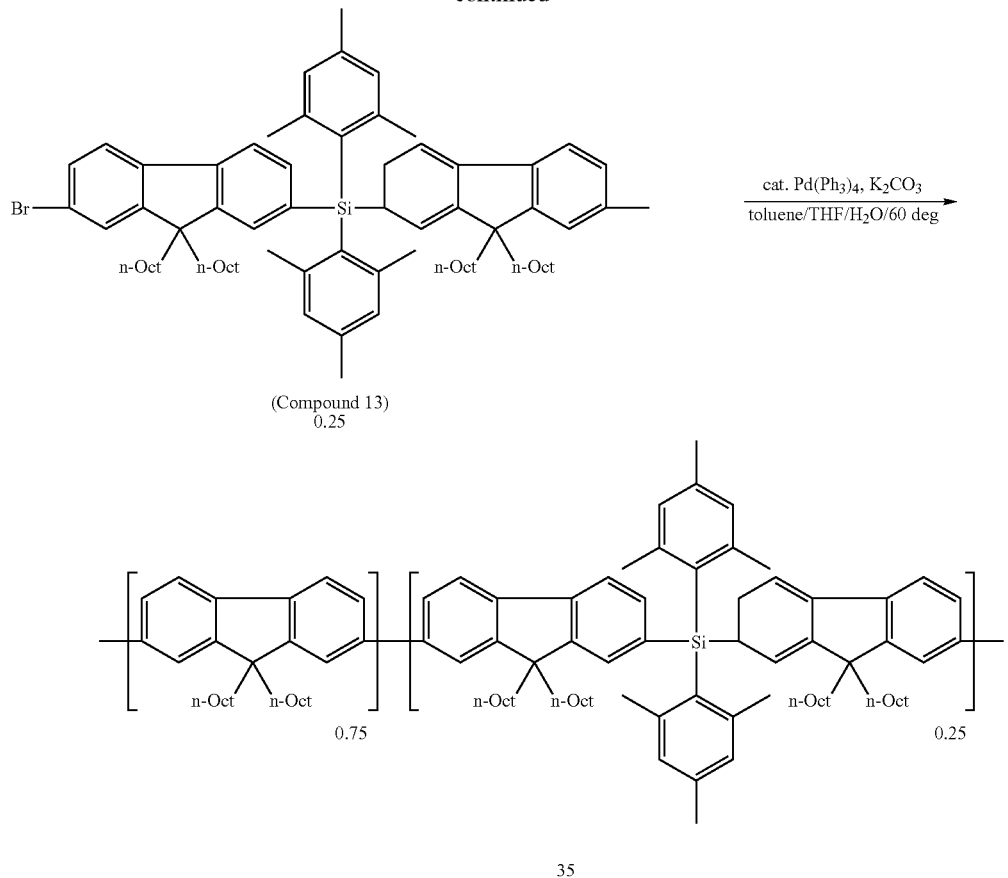

(Compound 13)
0.25

Under a nitrogen gas atmosphere, 704 mg (0.585 mm) of bis(7-bromo-9,9-dioctylfluorenyl)dimesitylsilane (compound 13), 750 mg (1.17 mmol) of 9,9-dioctylfluorene with boron structures introduced onto the 2 and 7 positions, 323 mg (0.589 mmol) of 2,7-dibromo-9,9-dioctylfluorene, 2.20 g (15.9 mmol) of potassium carbonate, 15 ml of THF and 8 ml of distilled water were added to a 100 ml three-necked flask equipped with a reflux condenser, and this mixture was heated to 60° C. After the dissolution of the substrate was confirmed, one full spatula of tetrakis(triphenylphosphine) palladium was added, and the mixture was heated and agitated for approximately 48 hours. When toluene was added following cooling and the solvent was distilled away as far as possible, a high-viscosity substance was obtained.

The substance thus obtained was washed with 1 N hydrochloric acid, a 1 N aqueous solution of sodium hydroxide and distilled water in that order, so that the potassium carbonate was removed. Furthermore, dissolution in a small amount of warm THF and re-precipitation from methanol was performed twice, and the product was purified by performing a Soxhlet extraction (acetone) for approximately 48 hours, thus producing an EL polymer containing repeating units represented by formula (7) (bisfluorenyldimesitylsilane) at the rate of 25 mol % and fluorene units represented by formula (2) at the rate of 75 mol % (amount yielded: 1.096 mg). As a result of GPC (eluent: THF, according to comparison with a standard polystyrene of known molecular weight), this polymer showed an Mw value (weight average molecular weight) of 20,290 and an Mn value (number average molecular weight) of 11,663. Furthermore, the concentration of inorganic metallic elements in this polymer was less than the detection limit (0.1%) of EDX (energy distribution type fluorescent X-ray measurement).

Comparative Example 1

A poly(9,9-dioctylfluorene) comprising only fluorene units represented by formula (2) was obtained by repeating the same operation as in Example 6, except for the fact that no bis(7-bromo-9,9-dioctylfluorenyl)diphenylsilane was used. This polymer showed a weight average molecular weight of 37,097.

Evaluation

It is known that the EL spectrum of an EL polymer shows more or less the same shape as the fluorescence spectrum of the polymer. Accordingly, the characteristics of the EL polymers were evaluated as described below by investigating the fluorescence spectrum showing a positive correlation with the EL spectrum, rather than directly evaluating the EL spectrum.

Measurement of Photoluminescence (Fluorescence) Spectra of EL Polymer Films

For each of the EL polymers of Examples 6 through 12 and Comparative Example 1, a toluene solution (0.5 wt %) of the polymer was applied as a coating to the surface of a quartz glass by means of a spin coater whose rotational speed was controlled, so that the dry thickness of the coating film was 100 nm. Following the application of this coating, the ultraviolet-visible absorption spectrum was measured, and the photoluminescence (fluorescence) spectrum in the case of excitation at the maximum absorption wavelength was measured. Next, the EL polymer film was heated for 1 hour at 50° C., then for 1 hour at 100° C., under reduced pressure (0.1 mmHg (13.3 Pa)), and was then returned to room temperature, after which similar measurements were made. The measurement results are shown in FIGS. 1 through 8.

In the case of the poly(9,9-dioctylfluorene) of Comparative Example 1, as is seen from the ultraviolet-visible absorption spectrum (fluorescence spectrum) shown in FIG. 1A, it was possible to confirm the emission of fluorescent light of excimer origin in the vicinity of 540 nm, which is a cause of deterioration in the color purity of the EL element.

Figure 5A:
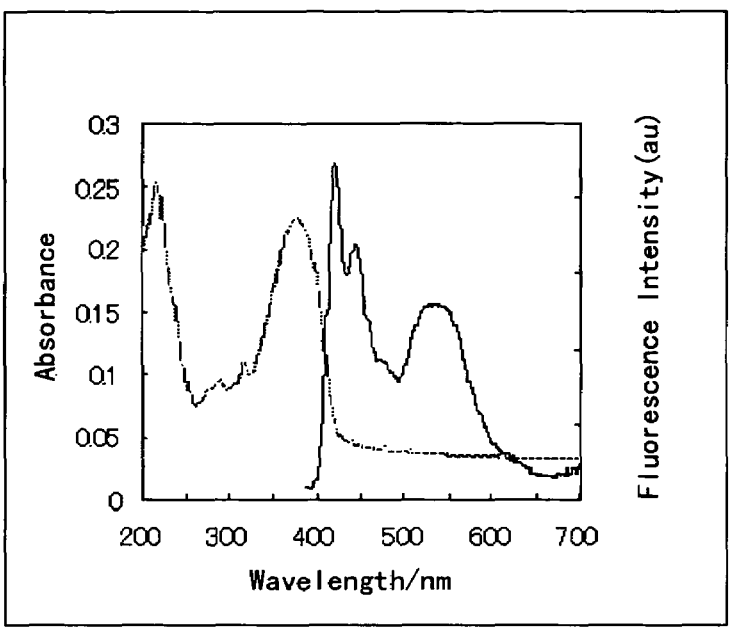
FIG. 5A shows the ultraviolet-visible absorption spectrum (fluorescent spectrum) of the EL polymer film of Example 9 (containing the repeating unit of formula (5) (bisfluorenyldimethylsilane) at the rate of 25 mol %) prior to heat treatment and FIG. 5B shows the ultraviolet-visible absorption spectrum (fluorescent spectrum) of the same film following heat treatment.
Figure 5B:
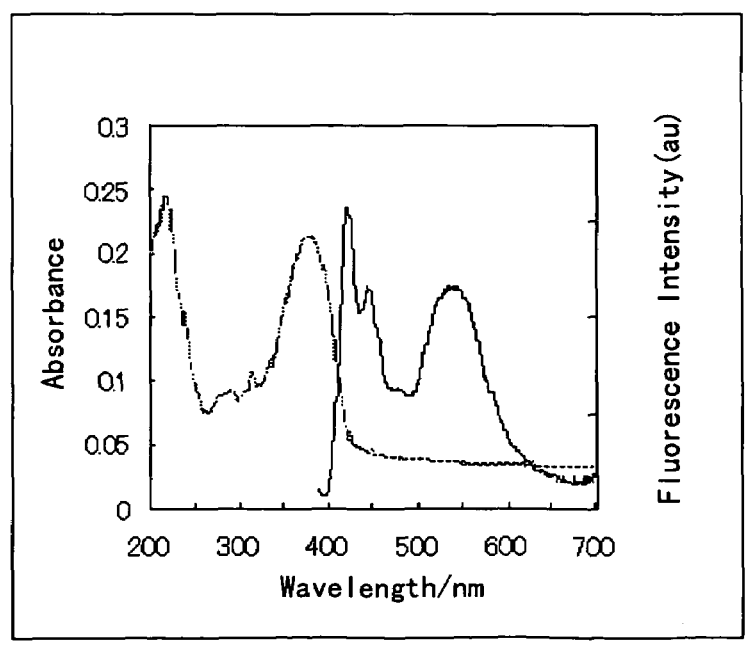
Figure 6A:
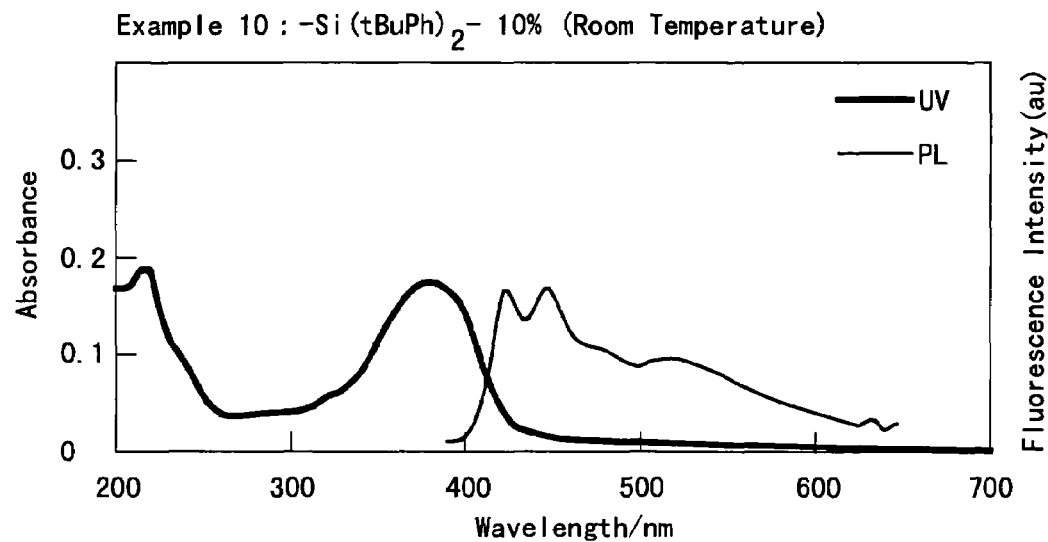
FIG. 6A shows the ultraviolet-visible absorption spectrum (fluorescent spectrum) of the EL polymer film of Example 10 (containing the repeating unit of formula (8) (bisfluorenyldi-t-butylphenylsilane) at the rate of 10 mol %) prior to heat treatment and FIGS. 6B and 6C show the ultraviolet-visible absorption spectra (fluorescent spectra) of the same film following heat treatment.
Figure 6B:
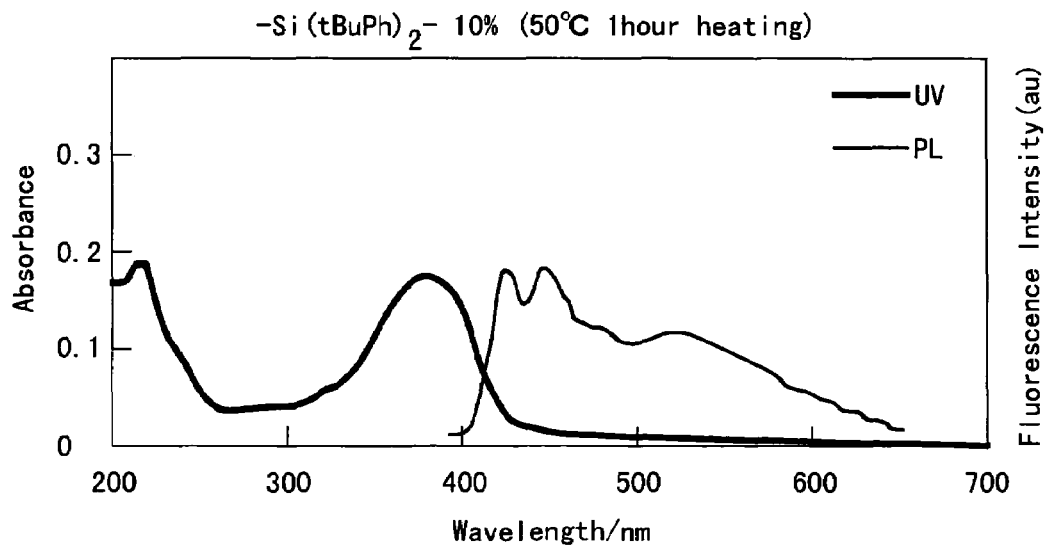
Figure 6C:
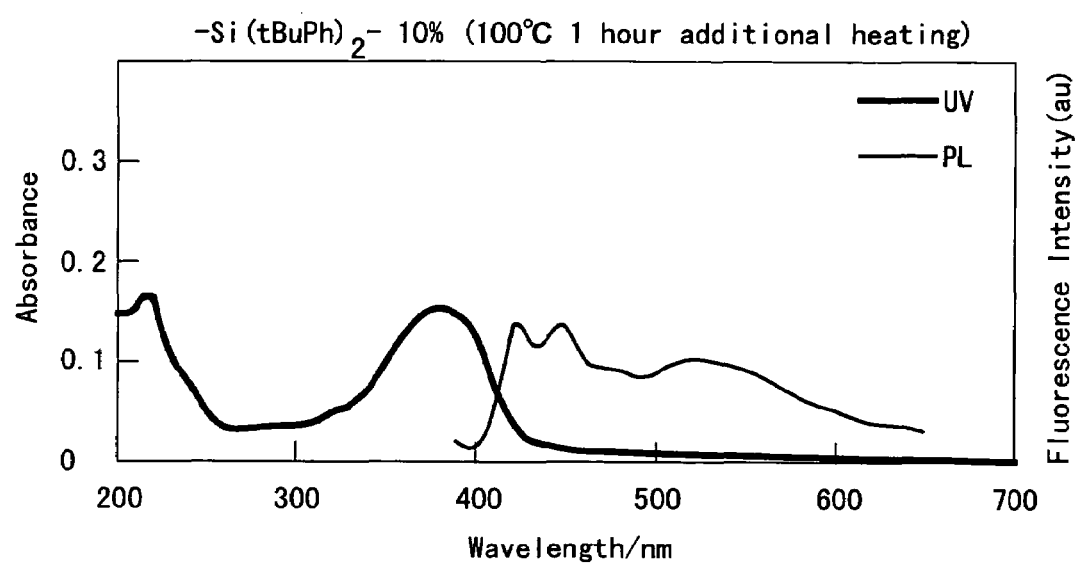
Figure 7A:
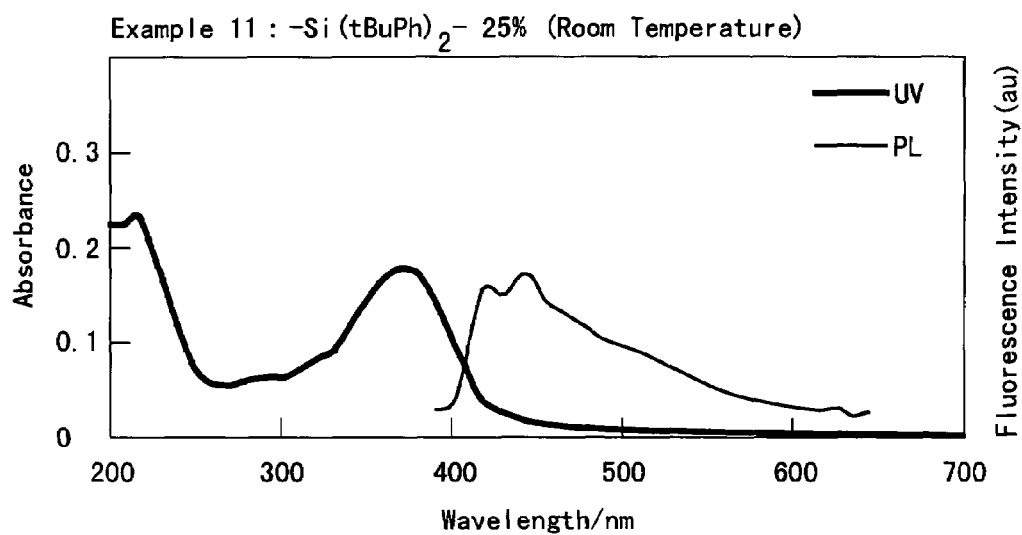
FIG. 7A shows the ultraviolet-visible absorption spectrum (fluorescent spectrum) of the EL polymer film of Example 11 (containing the repeating unit of formula (8) (bisfluorenyldi-t-butylphenylsilane) at the rate of 25 mol %) prior to heat treatment and FIGS. 7B and 7C shows the ultraviolet-visible absorption spectra (fluorescent spectra) of the same film following heat treatment.
Figure 7B:
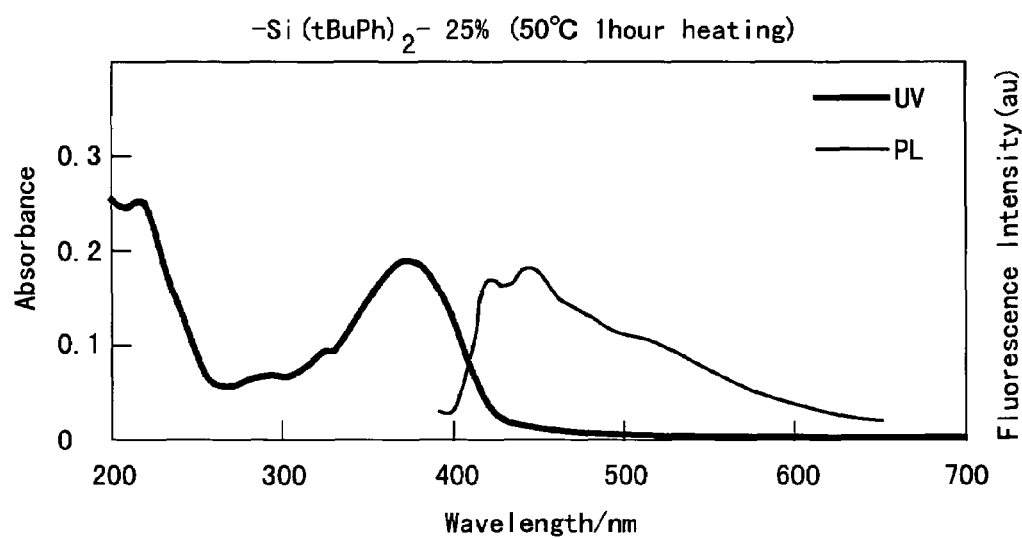
Figure 7C:
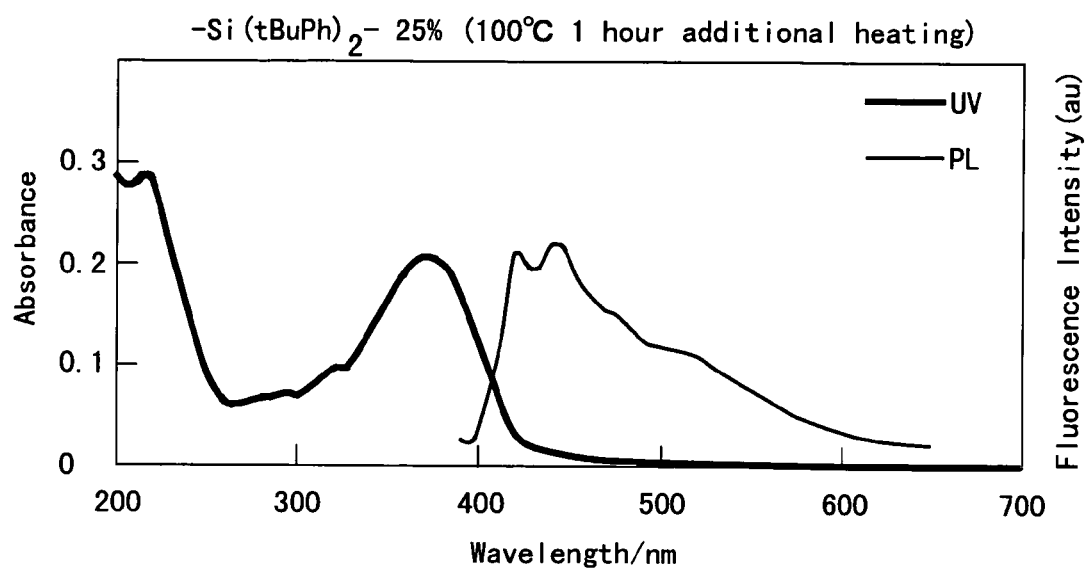
Figure 8A:
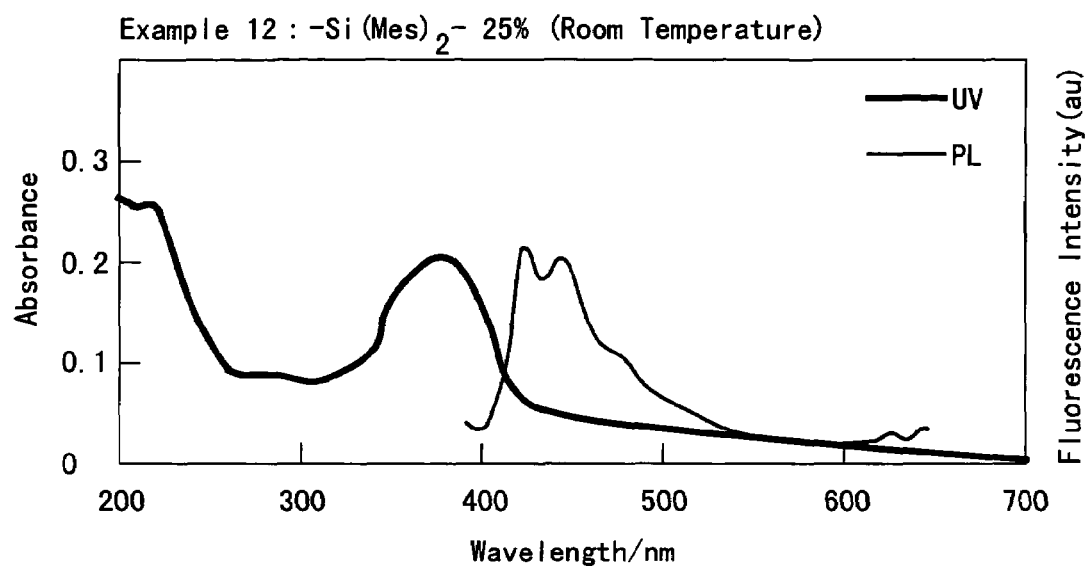
FIG. 8A shows the ultraviolet-visible absorption spectrum (fluorescent spectrum) of the EL polymer film of Example 12 (containing the repeating unit of formula (7) (bisfluorenyldimethylsilane) at the rate of 25 mol %) prior to heat treatment and FIGS. 8B and 8C show the ultraviolet-visible absorption spectra (fluorescent spectra) of the same film following heat treatment.
Figure 8B:
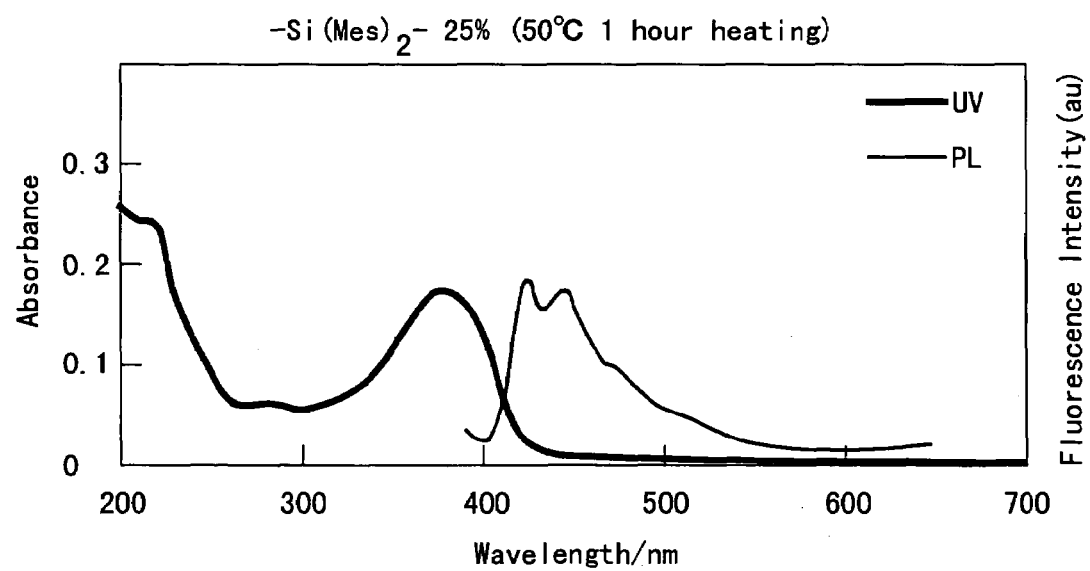
Figure 8C:
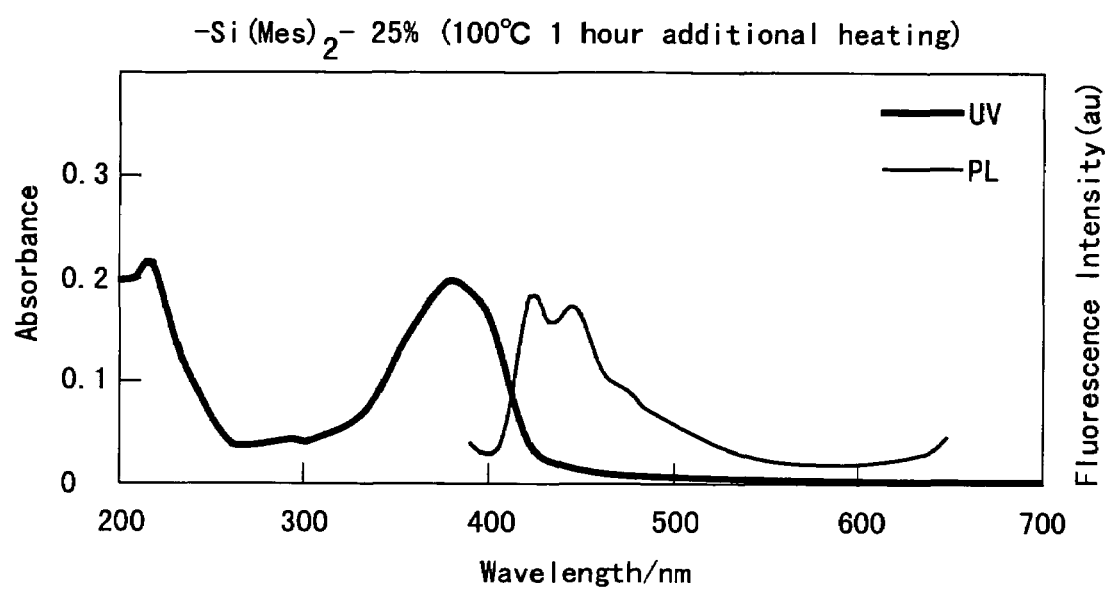

On the other hand, when the bisfluorene compound of formula (4) was copolymerized with the fluorene compound of formula (2) in EL polymers while increasing the content [of this bisfluorene compound] (0% (FIG. 1A)→10% (FIG. 2A)→25% (FIG. 3A)→50% (FIG. 4A), the emission of fluorescent light of excimer origin in the vicinity of 540 nm was suppressed. Similarly, when the bisfluorene compound of formula (8) was copolymerized while increasing the content of this compound (10% (FIG. 6A)→25% (FIG. 7A)), the emission of fluorescent light of excimer origin in the vicinity of 540 nm was suppressed. In particular, this suppressing effect was maintained even when a heat treatment was performed in order to promote excimer formation (see FIG. 2B in contrast to FIG. 2A, FIG. 3B in contrast to FIG. 3A, FIG. 4B in contrast to FIG. 4A, FIGS. 6B and 6C in contrast to FIG. 6A, FIGS. 7B and 7C in contrast to FIG. 7A, and FIGS. 8B and 8C in contrast to FIG. 8A). Specifically, the abovementioned poly(9,9-dioctylfluorene) showed a complete change in the shape of the spectrum before and after heat treatment (FIGS. 1A and 1B); however, in the case of polymers containing 25 mol % or more bisfluorenyldiphenylsilane, almost no change was seen (FIGS. 3A and 3B, FIGS. 4A and 4B), and excimer formation was also conspicuously suppressed in a polymer containing 25 mol % bisfluorenyldi-t-butylphenylsilane (FIG. 7) and a polymer containing 25 mol % bisfluorenyldimesitylsilane (FIG. 8). Furthermore, in terms of showing no change in the shape of the spectrum, bisfluorenyldimethylsilane was also effective, and was superior in terms of thermal stability (FIGS. 5A and 5B).

Manufacture of Organic EL Elements

A glass substrate covered with ITO (indium-tin oxide) [thickness 200 nm, sheet resistance 10 Ω/sq or less, transmissivity 80% or greater] was subjected to an ultrasonic treatment using a commercially marketed cleaning agent. Next, this substrate was rinsed with de-ionized water, and was then subjected to an ultrasonic treatment with acetone, followed by an ultrasonic treatment with IPA (isopropyl alcohol). Finally, this substrate was subjected to a degreasing treatment by boiling in IPA. Afterward, the substrate was exposed for several minutes using an excimer irradiation apparatus.

The surface of this substrate (ITO surface) was coated with a hole transporting polymer (Baytron P (TP AI 4083), manufactured by Bayer) filtered by a 0.45-μm PP filter using a spin coater whose rotational speed was controlled so that the dry film thickness was 70 nm. This coated substrate was then dried using a vacuum drier (100° C.×1 hour), so that a hole transporting polymer layer was formed.

Next, toluene solutions (0.5 wt %) of the respective EL polymers of Comparative Example 1, Example 6 and Example 7 were filtered by means of a 0.45-μm PTFE filter. Next, each of these polymer solutions was applied as a coating to the surface of the previously formed hole transporting layer by means of a spin coater whose rotational speed was controlled so that the dry film thickness was 100 nm, and this coating was dried so that a light-emitting layer was formed.

Calcium was vacuum-evaporated (at 10–6 Torr or less) on this light-emitting layer to a thickness of 20 nm, and aluminum was then similarly vacuum-evaporated to a thickness of 150 nm, so that a cathode layer was formed, thus producing an organic EL element.

Figure 9:
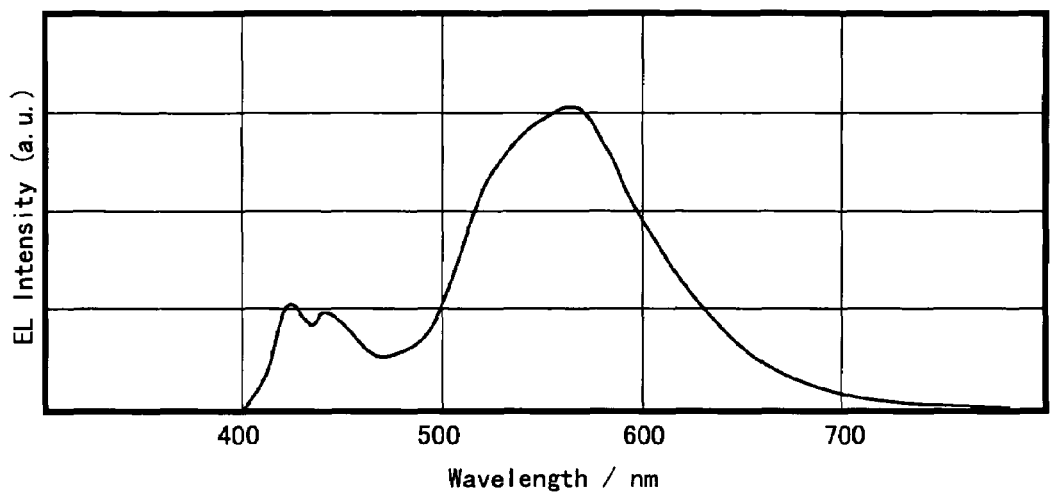
FIG. 9 shows the electroluminescence spectrum of an organic EL element using the poly(9,9-dioctylfluorene) of Comparative Example 1 as a light-emitting layer.
Figure 10:
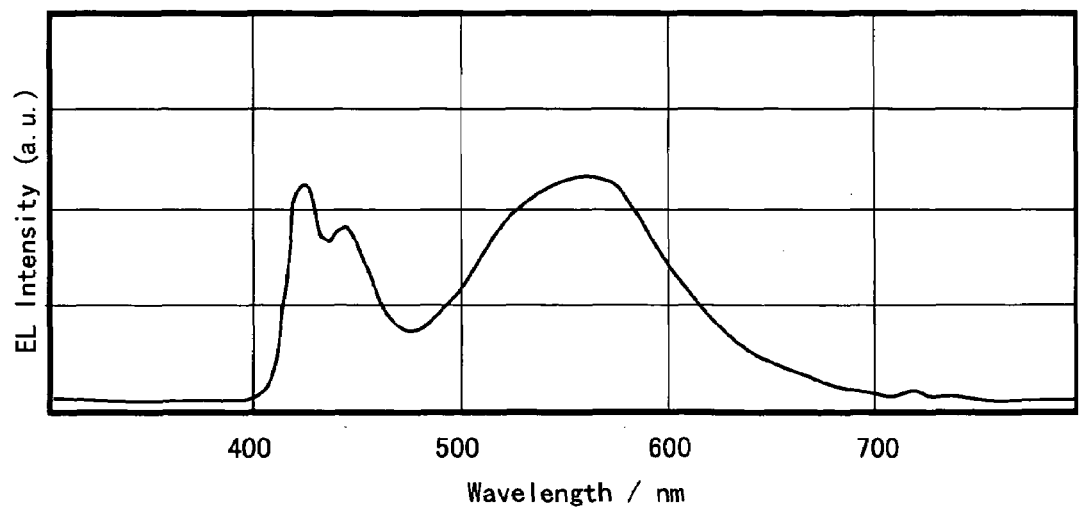
FIG. 10 shows the electroluminescence spectrum of an EL element using the EL polymer film of Example 4 (containing the repeating unit of formula (4) (bisfluorenyldiphenylsilane) at the rate of 10 mol %) as a light-emitting layer.
Figure 11:
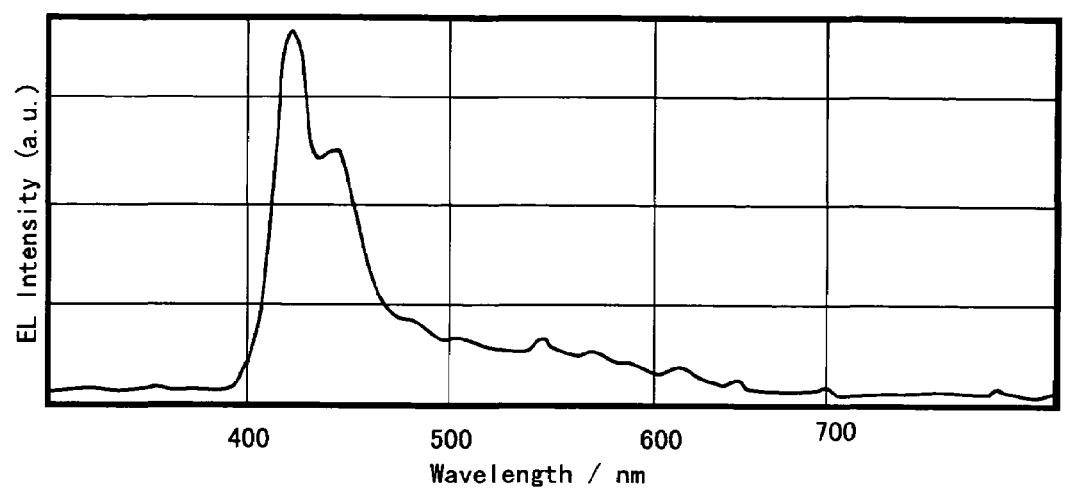
FIG. 11 shows the electroluminescence spectrum of an EL element using the EL polymer film of Example 5 (containing the repeating unit of formula (4) (bisfluorenyldiphenylsilane) at the rate of 25 mol %) as a light-emitting layer

When a positive polarity was applied to the ITO side of the organic EL element thus obtained, and a negative polarity was applied to the aluminum side, light emission corresponding to electroluminescence (EL) was confirmed (FIGS. 9, 10 and 11).

Furthermore, the electroluminescence (EL) spectrum obtained showed a good correspondence with the corresponding photoluminescence (fluorescence) spectrum (FIGS. 9 and 1A, FIGS. 10 and 2A, and FIGS. 11 and 3A).

INDUSTRIAL APPLICABILITY

In the present invention, a novel π-σ conjugated polymer in which the deterioration of the color purity of electroluminescence caused by excimer formation is greatly suppressed in spite of the fact that the polymer is a π-σ conjugated type fluorene polymer is provided. In particular, this novel π-σ conjugated polymer shows an extremely high color purity of blue emitted light.

The electroluminescent polymer of the present invention is useful as a light-emitting material for organic electroluminescent elements, and the bisfluorenylsilane compound of the present invention is useful as manufacturing method raw material for electroluminescent polymers.

What is claimed is:

1. An electroluminescent polymer with repeating units represented by formula (1)

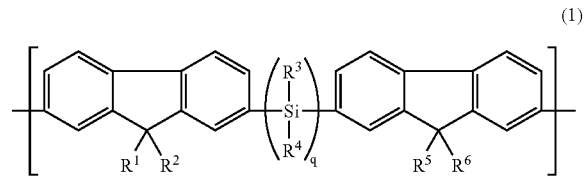

(1)

where $R^1$, $R^2$, $R^5$ and $R^6$ each independently indicate a hydrogen atom or substituent group, $R^3$ and $R^4$ each independently indicate an aryl group or alkyl group, and q is 2.

2. The electroluminescent polymer according to claim 1, wherein the substituent group that can be independently indicated by $R^1$, $R^2$, $R^5$ and $R^6$ in formula (1) is an alkyl group, alkenyl group, alkynyl group, aralkyl group, aryl group, heteroaryl group, alkoxy group, aryloxy group or aliphatic heterocyclic group.

3. The electroluminescent polymer according to claim 1, wherein $R^1$, $R^2$, $R^5$ and $R^6$ in formula (1) each independently indicate an alkyl group or aryl group, and $R^3$ and $R^4$ indicate an alkyl group.

4. The electroluminescent polymer according to claim 1, wherein $R^1$, $R^2$, $R^5$ and $R^6$ in formula (1) each independently indicate an alkyl group or aryl group, and $R^3$ and $R^4$ indicate methyl group.

5. The electroluminescent polymer according to claim 1, wherein $R^1$, $R^2$, $R^5$ and $R^6$ in formula (1) indicate n-octyl group, and $R^3$ and $R^4$ indicate methyl group.

6. The electroluminescent polymer according to claim 1, containing repeating units represented by formula (1) at the rate of 0.1 mol % or greater.

7. The electroluminescent polymer according to claim 1, further containing repeating units represented by formula (2)

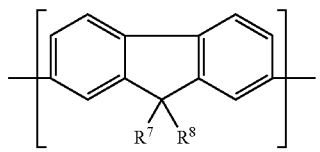

(2)

where $R^7$ and $R^8$ each independently indicate a hydrogen atom or a substituent group at the rate of 10 to 99.9 mol %.

8. The electroluminescent polymer according to claim 7, wherein $R^7$ and $R^8$ in formula (2) each independently indicate an alkyl group, alkenyl group, alkynyl group, aralkyl group, aryl group, heteroaryl group, alkoxy group, aryloxy group or aliphatic heterocyclic group.

9. The electroluminescent polymer according to claim 7, wherein $R^7$ and $R^8$ in formula (2) each independently indicate an alkyl group or aryl group.

10. The electroluminescent polymer according to claim 7, wherein $R^7$ and $R^8$ in formula (2) indicate n-octyl groups.

11. A bisfluorenylsilane compound represented by formula (3)

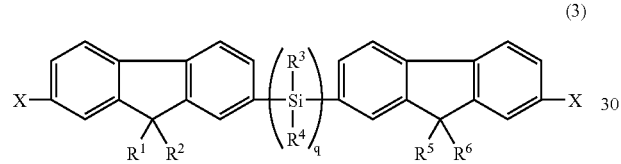

(3)

where $R^1$, $R^2$, $R^5$ and $R^6$ each independently indicate a hydrogen atom or substituent group, $R^3$ and $R^4$ each independently indicate an aryl group or alkyl group, q is 2, and X is a halogen atom.

12. The bisfluorenylsilane compound according to claim 11, wherein $R^1$, $R^2$, $R^5$ and $R^6$ in formula (3) each independently indicate an alkyl group, alkenyl group, alkynyl group, aralkyl group, aryl group, heteroaryl group, alkoxy group, aryloxy group or aliphatic heterocyclic group.

13. The bisfluorenylsilane compound according to claim 11, wherein $R^1$, $R^2$, $R^5$ and $R^6$ in formula (3) each independently indicate an alkyl group or aryl group, and $R^3$ and $R^4$ indicate an alkyl group.

14. The bisfluorenylsilane compound according to claim 11, wherein $R^1$, $R^2$, $R^5$ and $R^6$ in formula (3) each independently indicate an alkyl group or aryl group, and $R^3$ and $R^4$ indicate methyl group.

15. The bisfluorenylsilane compound according to claim 11, wherein $R^1$, $R^2$, $R^5$ and $R^6$ in formula (3) indicate an n-octyl group, $R^3$ and $R^4$ indicate methyl group, and X is bromine atom.

16. An organic electroluminescent element comprising a light-emitting layer made from the electroluminescent polymer according to claim 1 supported by a pair of electrodes sandwiching the same.

* * * * *